US010391635B2

(12) United States Patent
Berghofer et al.

(10) Patent No.: US 10,391,635 B2
(45) Date of Patent: Aug. 27, 2019

(54) POSITIONING A ROBOT

(71) Applicant: KUKA Deutschland GmbH, Augsburg (DE)

(72) Inventors: Jakob Berghofer, Munich (DE); Sven Brudniok, Langerringen (DE); Sebastian Lohmeier, Munich (DE); Martin Riedel, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 138 days.

(21) Appl. No.: 15/503,886

(22) PCT Filed: Aug. 13, 2015

(86) PCT No.: PCT/EP2015/001673
§ 371 (c)(1),
(2) Date: Feb. 14, 2017

(87) PCT Pub. No.: WO2016/023635
PCT Pub. Date: Feb. 18, 2016

(65) Prior Publication Data
US 2017/0274533 A1    Sep. 28, 2017

(30) Foreign Application Priority Data

Aug. 14, 2014  (DE) .......................... 10 2014 012 124
Aug. 14, 2014  (DE) .......................... 10 2014 012 160

(51) Int. Cl.
*B25J 9/16*       (2006.01)
*B25J 9/00*       (2006.01)
(Continued)

(52) U.S. Cl.
CPC ............ *B25J 9/1689* (2013.01); *A61B 34/30* (2016.02); *A61B 34/37* (2016.02); *A61B 34/70* (2016.02);
(Continued)

(58) Field of Classification Search
CPC . B25J 9/0078; B25J 9/06; B25J 9/0051; B25J 9/1633; B25J 9/0009; B25J 9/0084;
(Continued)

(56) References Cited

U.S. PATENT DOCUMENTS 5,156,062 A * 10/1992 Appleberry .......... B25J 17/0266
74/490.01
5,539,291 A *  7/1996 Reboulet ................. B25J 9/107
318/568.11
(Continued)

FOREIGN PATENT DOCUMENTS

CN      102196776 A     9/2011
CN      102421387 A     4/2012
(Continued)

OTHER PUBLICATIONS

German Patent Office; Office Action in German Patent Application No. 10 2014 012 160.7 dated Jul. 29, 2015; 8 pages.
(Continued)

*Primary Examiner* — Thai T Dinh
(74) *Attorney, Agent, or Firm* — Dorton & Willis, LLP

(57) ABSTRACT

A positioning device for a robot includes an end effector, in particular a surgical end effector, which has a base and a flange to which the robot can be secured, wherein the flange is connected to the base by a kinematic system which has at least two joints. The flange can be adjusted from a first position relative to the base, in particular at least substantially on a circular path or straight line, to a second position by the kinematic system, the second position being spaced apart from the first position. An orientation means reorients the flange from a first orientation in the first position into a second orientation in the second position, the second orientation being rotated about a reference axis by at least 75 degrees, in particular relative to the first orientation, as a
(Continued)

result of an adjustment from a first position into a second position.

25 Claims, 10 Drawing Sheets

(51) Int. Cl.
*A61B 34/30* (2016.01)
*A61B 90/50* (2016.01)
*A61B 34/37* (2016.01)
*A61B 34/00* (2016.01)
*A61B 17/00* (2006.01)

(52) U.S. Cl.
CPC ............. *A61B 90/50* (2016.02); *B25J 9/0009* (2013.01); *B25J 9/0084* (2013.01); *A61B 2017/00477* (2013.01); *A61B 2090/506* (2016.02); *G05B 2219/39022* (2013.01)

(58) Field of Classification Search
CPC ........ B25J 9/126; B25J 9/1664; B25J 9/1689; A61B 34/20; A61B 90/50; A61B 34/70; A61B 34/30
See application file for complete search history.

(56) References Cited

U.S. PATENT DOCUMENTS

| | | | |
|---|---|---|---|
| 5,949,209 A | 9/1999 | Okamoto et al. | |
| 10,000,248 B1* | 6/2018 | Urata | B62D 57/032 |
| 10,166,684 B2* | 1/2019 | Brogardh | B25J 17/0266 |
| 2001/0013764 A1* | 8/2001 | Blumenkranz | B25J 9/1689 |
| | | | 318/568.11 |
| 2004/0261179 A1 | 12/2004 | Blumenkranz | |
| 2008/0295637 A1* | 12/2008 | Lessard | B25J 17/0266 |
| | | | 74/490.05 |
| 2010/0069920 A1 | 3/2010 | Naylor et al. | |
| 2010/0228264 A1 | 9/2010 | Robinson et al. | |
| 2011/0245844 A1 | 10/2011 | Jinno | |
| 2011/0277775 A1* | 11/2011 | Holop | A61B 17/3423 |
| | | | 128/849 |
| 2013/0057004 A1* | 3/2013 | Murata | B25J 15/0009 |
| | | | 294/106 |
| 2015/0108099 A1* | 4/2015 | Ferrero | B23K 11/314 |
| | | | 219/86.33 |
| 2016/0120611 A1* | 5/2016 | Lohmeier | A61B 90/50 |
| | | | 606/130 |

FOREIGN PATENT DOCUMENTS

| | | |
|---|---|---|
| DE | 3601437 A1 | 7/1986 |
| DE | 10013721 A1 | 9/2001 |
| DE | 10357609 A1 | 7/2005 |
| DE | 102008037239 A1 | 2/2010 |
| DE | 102012015541 A1 | 2/2014 |
| DE | 102013004459 A1 | 6/2014 |
| EP | 2578177 A2 | 4/2013 |
| JP | 2003341834 A | 12/2003 |
| WO | 2010130817 A1 | 11/2010 |
| WO | 2014000041 A1 | 1/2014 |

OTHER PUBLICATIONS

German Patent Office; Search Report in German Patent Application No. 10 2014 012 160.7 dated Jul. 16, 2015; 10 pages.
German Patent Office; Office Action in German Patent Application No. 10 2014 012 124.0 dated Jun. 15, 2015; 12 pages.
German Patent Office; Search Report in German Patent Application No. 10 2014 012 124.0 dated May 22, 2015; 10 pages.
European Patent Office; Search Report in International Patent Application No. PCT/EP2015/001673 dated Nov. 11, 2015; 4 pages.
Chinese Patent Office; Examination Report in Chinese Patent Application No. 201580043600.9 dated Jul. 3, 2018; 5 pages.
Chinese Patent Office; Search Report in Chinese Patent Application No. 201580043600.9 dated Jun. 26, 2018; 2 pages.

* cited by examiner

POSITIONING A ROBOT

CROSS-REFERENCE

This application is a national phase application under 35 U.S.C. § 371 of International Patent Application No. PCT/EP2015/00673, filed Aug. 13, 2015 (pending), which claims the benefit of German Patent Application No. DE 10 2014 012 160.7 filed Aug. 14, 2014 (pending), and German Patent Application No. DE 10 2014 012 124.0 filed Aug. 14, 2014 (pending), the disclosures of which are incorporated by reference herein in their entirety.

TECHNICAL FIELD

The present invention relates to a device and a method for positioning a robot of a robot arrangement, and a robot arrangement with such a device.

BACKGROUND

Surgical robots are provided for moving a surgical end effector, for example, a scalpel, forceps, camera, or hose opening, on or in patients relative to a surgical robot base, in that drives of the surgical robot move its joints.

According to in-house practice, ceiling or floor-mounted surgical robots are known, in which one first or base axis of rotation of the surgical robot is arranged substantially vertical. Wall-mounted surgical robots are also known, in which the base axis of rotation of the surgical robot is instead arranged substantially horizontal.

In particular, in order to optimally use the kinematic system of the surgical robot and/or the available space, and/or to prevent interferences with additional surgical robots, positioning devices are additionally known according to proprietary practice in order to reposition the surgical robot base prior to the operation and, if necessary, during the operation.

The operation of such a positioning device is, however, difficult, in particular for medical personnel without corresponding kinematic knowledge.

SUMMARY

The present invention is subsequently described in particular with respect to a surgical robot, for which the invention is particularly advantageous. The invention may, however, also be advantageously used for industrial and/or service manipulators, in particular industrial and/or service robots, and is therefore not limited to surgical robots.

One object of the present invention is to improve the positioning of a robot, in particular a surgical robot.

According to one aspect of the present invention, a carrier system for a manipulator or a carrier system for a manipulator arrangement with a manipulator comprises a carrier and a flange to which the manipulator is securable or is secured, in particularly detachably, for example, electromagnetically, hydraulically, and/or by using screws. In one embodiment, the manipulator is a robot, in particular a surgical, industrial, or service robot.

In one embodiment, the flange is fixedly connected to the carrier or is designed to be immobile relative to the same, in particular, is designed integrally with the same. In another embodiment, the flange, or the manipulator secured thereto, is adjustable relative to the carrier, in particular is displaceable and/or rotatable about one axis or multiple axes, in particular vertically and/or horizontally, for example, by a lifting column and/or a rotary joint.

In one embodiment, the flange of the carrier system is the positioning device flange of a positioning device, described subsequently in greater detail, according to another aspect of the present invention, and the carrier of the carrier system is the carrier for this positioning device, on which the positioning device base is mounted to be linearly moveable about one or multiple axes and/or rotatable, wherein the manipulator or surgical robot is securable or is secured to the positioning device flange of the positioning device. Correspondingly, in one embodiment, the subsequently described positioning device comprises, in particular, the carrier system described here. As described at the beginning, this system may, however, likewise also be used independently from this, in particular for or with an industrial or service manipulator, in particular an industrial or service robot.

According to one aspect of the present invention, the carrier system comprises an air chamber arrangement, arranged on the carrier, in particular detachably or permanently connected to the carrier, with one or more pressure chambers which are surrounded by a pressure apron.

According to one aspect, the air chamber arrangement, in particular one or more of its pressure chambers, is connectable to a compressed air supply to form a single-cell or multi-cell air cushion, in particular, the air chamber arrangement, in particular one or more of its pressure chambers, is connected to a compressed air supply to form a single-cell or multi-cell air cushion.

Thus, the carrier system may be advantageously moved, in particular manually moved, in particular moved precisely, with low noise, low friction, and/or low wear and/or over obstacles like hoses, thresholds, or the like, in particular with the manipulator secured to the flange or, for example, to change the manipulator, also without a manipulator secured to the flange.

In one embodiment a common pressure apron surrounds two or more, in particular all pressure chambers of the air chamber arrangement. Thus, a compact and/or advantageous design may be achieved. In one embodiment, the air chamber arrangement comprises at least two pressure aprons which respectively surround one or more pressure chambers of the air chamber arrangement, or at least two pressure chambers are surrounded by different pressure aprons. Thus, an increased reliability and/or replaceability may be advantageously achieved.

In one embodiment, a pressure apron surrounds a pressure chamber circumferentially; this pressure chamber is thus open toward the ground. In one embodiment, a pressure apron is flexible, for example, made from a rubber or an in particular coated textile material, or an elastic plastic material. Correspondingly, a pressure chamber comprises in one embodiment a variable volume, which preferably increases for moving the carrier or to form the air cushion, and/or is decreased to fix the carrier by means of negative pressure. The pressure chamber in one embodiment is correspondingly delimited or formed circumferentially by the pressure apron, and on the top by a bottom of the carrier and/or a part of the pressure apron arranged thereon.

Due to the compressed air which discharges through a gap between the floor and the pressure apron(s), a disturbing noise may result and/or particles, in particular dust, may be swirled up, in particular stirred up from the floor in particular in the case of a single-cell or multi-celled air cushion, which carries the carrier, in particular with the manipulator connected thereto, and which is formed by the pressure chamber(s) connected to the compressed air supply. Likewise, noises may result during a negative pressure fixing the carrier due to surrounding air being sucked into the pressure chamber(s). This is disadvantageous, in particular, during use as a carrier system of a surgical robot arrangement.

Therefore, the air chamber arrangement in one embodiment comprises at least one sound chamber circumferentially surrounding at least one of the pressure chambers, the sound chamber being surrounded by an acoustic apron.

In one embodiment, a common acoustic apron surrounds two or more, in particular all pressure chambers or pressure aprons of the air chamber arrangement, preferably concentrically. Thus, a compact and/or advantageous design may be achieved. In one embodiment, the air chamber arrangement comprises at least two acoustic aprons which respectively surround, preferably concentrically, one or more pressure chambers or pressure aprons of the air chamber arrangement, or at least two pressure chambers or pressure aprons are surrounded preferably concentrically by different acoustic aprons or sound chambers. Thus, an increased reliability may be advantageously achieved.

In one embodiment, an acoustic apron surrounds one or more pressure aprons or pressure chambers circumferentially, the corresponding sound chamber is thus open toward the bottom. In one embodiment, an acoustic apron is flexible, for example, made from rubber or an in particular coated textile material, or an elastic plastic material. Correspondingly, in one embodiment, a sound chamber likewise comprises a variable volume, which increases or decreases with the volume of the pressure chamber(s). In one embodiment, a sound chamber is correspondingly delimited or formed circumferentially inwardly by the pressure apron(s), outwardly by the acoustic aprons, and on the top by a bottom of the carrier and/or a part of the pressure apron(s) or acoustic apron(s) arranged thereon.

In one embodiment, at least one acoustic apron and pressure apron are designed integrally with one another, which may improve production and/or assembly. In another embodiment, at least one acoustic apron and pressure apron are designed separately from one another, which may improve the design and/or replacement.

In one embodiment, during a movement of the carrier and/or in the case of a fixed carrier, a pressure and/or sound apron sits sealingly on the floor or substrate or is provided or equipped for this purpose. For this purpose, an apron may comprise a preferably flexible, floor-side sealing element, for example a sealing lip or the like. Additionally or alternatively, the apron may be biased, in particular elastically against the floor or substrate.

In one embodiment, a pressure and/or acoustic apron is formed by one or more concentric rows, in particular of lamellae, overlapping one another, distributed across the circumference. Likewise, a pressure and/or acoustic apron may also be formed, for example by a single- or multi-layer solid wall.

In one refinement, the carrier system comprises at least one sound damping means for damping airborne sound in at least one sound chamber. The sound damping means may comprise in particular one or more reflected sound dampers with multiple, in particular with at least four chambers which communicate with one another with cross-section expansions and/or reductions; in one embodiment, baffle walls inclining toward one another are arranged therein, and/or have one or more, in particular lamellar absorption sound dampers, preferably with porous material, in particular non-woven fabric, woven fabric, fiberglass wool and/or fiberglass fibers.

Thus, vibrations of the compressed air, which discharges out of a gap between the pressure apron(s) and the floor into a sound chamber to form the air cushion, and/or vibrations of surrounding air, which is sucked in as a result of a negative pressure fixing the carrier, are advantageously damped and thus sound emissions and/or particle swirling is reduced.

In one refinement, a sound damping means is arranged in a sound chamber. Thus, airborne sound and/or particle swirling may be advantageously reduced close to the originating point. In particular, one or more concentric rows of lamellae may be arranged in one sound chamber, which during operation, in particular during the formation of air cushions, preferably drag on the floor and/or comprise sound absorbing material like, for example, textile non-woven fabric, woven fabric, or the like. Additionally or alternatively, the acoustic apron may be formed by such lamellae.

Additionally or alternatively, a sound damping means may be spaced apart from a sound chamber and may communicate with this sound chamber in particular via an air passage, in particular an air duct. Thus, the sound damping means may be arranged at an advantageous location.

Such a sound damping means, spaced apart from a sound chamber and communicating with the same, may—like a sound damping means arranged in the sound chamber—be fixed to the carrier or on the carrier side. Thus, for example, compressed air, which discharges out of a pressure chamber into a sound chamber through a gap between the floor and pressure apron, may flow through or around sound absorbing lamellae in the sound chamber before it is discharged, sounds damped, into the surroundings through a gap between the floor and the acoustic apron, preferably likewise formed as lamellae. Likewise, the air may be diverted out of the sound chamber into a carrier-fixed sound damping means, out of which the air may discharge close to or away from the floor to reduce swirling up of floor dust.

In another embodiment, a sound damping means, spaced apart from a sound chamber and communicating with the same is a sound damping means that is apart from or external to the carrier, and communicates with the sound chamber preferably via an air duct arising from the carrier. The carrier-external sound damping means may thus guide the air into the surroundings at a point removed from the carrier. In one embodiment, such a carrier-external sound damping means is stationary or fixed in the surroundings; in another embodiment, it is likewise moveable or mobile.

According to one aspect of the present invention for moving the carrier, one or more pressure chambers of the air chamber arrangement are supplied from a compressed air supply connected to the same, or charged with air under negative pressure, and the carrier, borne by this means by air cushions, moves, in particular moves manually or is motor driven.

In order to securely fix the carrier, according to another aspect of the present invention, which may be combined with the air cushion aspect described here, a negative pressure is formed, in particular instead of an air cushion, in one or more pressure chambers of the air chamber arrangement through a negative pressure supply connected thereto, fixing the carrier. Correspondingly, the carrier system comprises according to one aspect of the present invention a compressed air supply, connectable, in particular connected, to one or more pressure chambers of the air chamber arrangement, for supplying compressed air, and/or a negative pressure supply, connectable, in particular connected, to one or more, in particular the same or different pressure chambers of the air chamber arrangement, for forming a negative pressure fixing the carrier.

As previously indicated, in one embodiment, one or more pressure chambers of the air chamber arrangement may thereby be selectively connected to the compressed air supply or negative pressure supply in order to form a cell of an air cushion or alternatively a negative pressure fixing the carrier to the substrate. Thus, the air chamber arrangement may be advantageously designed to be more compact.

Similarly, the air chamber arrangement may also comprise one or more pressure chambers which are connectable, in particular are connected, only to the compressed air supply, and one or more pressure chambers, different from these, which are connectable, in particular are connected, only to the negative pressure supply. Thus, the carrier may be advantageously carried on air cushions or fixed on the substrate.

Similarly, as likewise already described, the air chamber arrangement according to one aspect may be connectable, in particular may be connected, only to a compressed air supply for forming an air cushion, or may be connectable, in particular may be connected, only to a negative pressure supply for fixing to a substrate. For example, a carrier moveable on wheels, rollers, rails, or by sliding may be fixable, in particular may be fixed to the substrate, by negative pressure in the air chamber arrangement. Nevertheless, the selective use of the air chamber arrangement as air cushions or for fixing provides a particularly advantageous double use.

In one embodiment, the compressed air supply and/or the negative pressure supply comprises a an air duct connection, fixed to the carrier or on the carrier side, which is connectable, in particular is connected, to a compressed air source or negative pressure source which is removed from the carrier or external to the carrier, and is itself in particular stationary or mobile. In particular, a compressed air supply and/or a negative pressure supply in the meaning of the present invention may be such an air duct connection, fixed to the carrier or on the carrier side, preferably in connection to the compressed air source or negative pressure source which is removed from the carrier or external to the carrier. Thus, the carrier may be disencumbered. Additionally or alternatively, the compressed air supply and/or the negative pressure supply may comprise a compressed air source or a negative source fixed to the carrier or on the carrier side. Thus, the carrier may be, at least partially, autonomously operated.

In one embodiment, a carrier-side and/or a carrier-external compressed air source comprises a pressure accumulator in which air under pressure with respect to the surroundings ("compressed air") is stored. Correspondingly, in one embodiment, a carrier-side and/or a carrier-external negative pressure source may comprise a pressure accumulator in which a negative pressure prevails with respect to the surroundings.

Additionally or alternatively, in one embodiment, a carrier-side and/or a carrier-external compressed air source comprises a turbomachine for increasing the pressure of air, in particular surrounding air, sucked in by the turbomachine, in particular a compressor. Correspondingly, in one embodiment, a carrier-side and/or a carrier-external negative pressure source may comprise a turbomachine for reducing the pressure of air, in particular surrounding air or air from the air chamber arrangement, sucked in by the turbomachine, in particular a compressor, for sucking in air from the air chamber arrangement or a Venturi nozzle connected to the compressor for sucking in air from the air chamber arrangement.

Correspondingly, for a more compact presentation, a pressure accumulator, in which negative pressure prevails with respect to the surroundings, and a turbomachine for generating negative pressure with respect to the surroundings are referred to as a negative pressure/compressed air source or a negative pressure/compressed air supply. For a more compact representation, both a compressed air supply and also a negative pressure supply are generally designated as a compressed air supply, a compressed air source and a negative pressure source are generally designated as a compressed air source.

In one embodiment, the compressed air supply and negative pressure supply may comprise the same air duct connection for selective or alternative connection to a carrier-external compressed air source or negative pressure source, and/or the same turbomachine, selectively inversely operated. Thus, the compressed air supply may be designed more compactly. Likewise, in one embodiment, the compressed air supply and negative pressure supply may comprise different air duct connections for, in particular, parallel connection to a carrier-external compressed air source or negative pressure source and/or two turbomachines. The compressed air supplies may thus be advantageously optimized and/or used in parallel.

In one embodiment, the carrier system comprises a roller arrangement with two or more transport rollers for moving the carrier. Thus, in particular, the carrier may continue to be moved during a drop or failure of the air cushion. The roller arrangement comprises three or four transport rollers in one refinement.

When the air cushion is formed, the roller arrangement is preferably spaced apart from the floor in order to fully exploit the advantages of the supporting air cushion. In one embodiment, the air cushion or the pressure apron(s), when the air cushion is formed, have a vertical extension which is greater than the vertical extension of the roller arrangement so that the roller arrangement is lifted from the floor when the air cushion is formed.

Additionally or alternatively, in one embodiment, the roller arrangement may be displaced, in particular pivoted or retracted, from an operating into a storage position, in particular autonomously and/or manually, preferably by or after the formation of the air cushion and/or by or prior to the formation of the negative pressure. Additionally or alternatively, the roller arrangement may be displaced, in particular pivoted or extended from the storage into the operating position, in particular autonomously and/or manually, preferably by or prior to the reduction of the air cushion and/or by or after the reduction of the negative pressure.

Additionally or alternatively, in one embodiment, the roller arrangement is connectable, in particular is connected, detachably to the carrier. In another embodiment, the roller arrangement is, in contrast, arranged stationarily or permanently on the carrier.

In one embodiment, the roller arrangement is arranged in one or more of the pressure chambers, which facilitates a particularly space-saving and advantageous static support.

In one embodiment, the carrier system comprises a support arrangement with two or more, in particular, elastic supports for supporting the carrier, in particular instead of the air cushion. As previously described with respect to the roller arrangement, to which the support arrangement may be provided alternatively or additionally, the support arrangement is preferably spaced apart from the floor when the air cushion is formed. In one embodiment, the air cushion or the pressure apron(s) have a vertical extension when the air cushion is formed which is greater than the vertical extension of the support arrangement, so that the support arrangement is lifted from the floor when the air cushion is formed. The carrier fixed by negative pressure is supported by the roller arrangement and/or the support arrangement in one embodiment.

Additionally or alternatively, in one embodiment, the support arrangement may be displaced, in particular pivoted or retracted, from an operating into a storage position, in particular autonomously and/or manually, preferably by or after the formation of the air cushion. Additionally or alternatively, the support arrangement may be displaced, in particular pivoted or extended from the storage into the operating position, in particular autonomously and/or manually, preferably by or prior to the reduction of the air cushion and/or by or prior to the formation of the negative pressure.

Additionally or alternatively, in one embodiment, the support arrangement may be connectable, in particular is connected, detachably to the carrier. In another embodiment, the support arrangement is, in contrast, arranged stationarily or permanently on the carrier.

In one embodiment, the carrier system has a controller and/or an operating device, in particular communicating therewith, for, in particular, the controlled supply of one or more pressure chambers with compressed air by the compressed air supply and/or for, in particular, the alternative supply with negative pressure by the negative pressure supply.

In one embodiment, the operating device is arranged on the carrier, in particular on a handle for moving the carrier, for example in the form of one or more actuation switches, buttons, or the like. Thus, the air cushion for moving the carrier or the negative pressure for fixing the carrier may be advantageously controlled, in particular activated and/or deactivated. Additionally or alternatively, the operating device may also be a remote operating device for controlling the air cushion or the negative pressure at a distance from the carrier, which remote operating device is connectable, in particular is connected, detachably to the carrier in one refinement.

In one embodiment, the controller comprises one or more, in particular steplessly adjustable and/or electrically actuated control valves for selectively supplying one or more pressure chambers with compressed air and/or negative pressure by the compressed air supply or negative pressure supply, and/or a controller for regulating these valves and/or a turbomachine of the compressed air supply and/or the negative pressure supply. In one refinement, the controller is equipped, in particular via software or programming, to supply one or more pressure chambers, in particular jointly or independently from one another, with compressed air and/or negative pressure through the compressed air supply and/or the negative pressure supply. In one refinement, the controller is equipped, in particular via software or programming, to regulate the compressed air pressure and/or negative pressure in the pressure chamber(s) to a predefined level, in that the controller regulates the same or supplies the same with compressed air or negative pressure through the compressed air supply and/or the negative pressure supply, based on a detected actual and a predefined target state, for example of the air pressure or of the vertical distance of the carrier to the floor.

In one embodiment, the controller regulates a supply of the air chamber arrangement, in particular one or more of its pressure chambers, with compressed air and/or negative pressure by compressed air supply and/or the negative pressure supply connected thereto, in particular an air supply and/or air removal or an overpressure and/or negative pressure in one or more pressure chambers of the air chamber arrangement on the basis of a tilting moment of the carrier system about the horizontal, or may be equipped for this purpose.

In one embodiment, the controller increases an overpressure or negative pressure in one or more of the air chambers of the air chamber arrangement if a tilting moment of the carrier system increases about the horizontal, and/or reduces an overpressure or negative pressure in one or more of the air chambers of the air chamber arrangement when a tilting moment of the carrier system about the horizontal decreases, or is equipped for this purpose.

In one embodiment, the controller increases an overpressure in one or more of the air chambers in such a way that this overpressure induces a counter moment to the tilting moment, thus, in particular in air chambers on one side of the carrier, on which the tilting moment of the carrier system seeks to tilt, and/or increases a negative pressure in one or more of the air chambers in such a way that this negative pressure induces a counter moment to the tilting moment, thus, in particular in air chambers on one side of the carrier, which seeks to lift the tilting moment of the carrier system, or is equipped for this purpose.

Likewise, the controller may increase the overpressure and/or negative pressure in all air chambers if a tilting moment of the carrier system about the horizontal increases, and/or reduce the overpressure or negative pressure in all air chambers of the air chamber arrangement if a tilting moment of the carrier system about the horizontal decreases, or is equipped for this purpose.

A tilting moment of the carrier system about the horizontal, i.e., a rotating moment which affects the carrier system and seeks to rotate or tilt the carrier system about a horizontal axis, depends, in particular, on a pose of a manipulator secured to the carrier: If the manipulator has a large extension and a center of gravity correspondingly spaced apart from the center of gravity of the carrier system, then this induces a tilting moment. Therefore, in one embodiment, the controller regulates the supply of the air chamber arrangement with compressed air and/or negative pressure based on a pose of the manipulator secured on the carrier system, or is equipped for this purpose. In one embodiment, the controller increases an overpressure or negative pressure in one or more of the air chambers of the air chamber arrangement if an extension of the manipulator increases, and/or reduces an overpressure or negative pressure in one or more air chambers of the air chamber arrangement if an extension of the manipulator decreases, or is equipped for this purpose. In one embodiment, the controller increases an overpressure in one or more air chambers on one side of the carrier on which the manipulator has an extension, and/or increases a negative pressure in one or more air chambers on a side opposite the extension, or is equipped for this purpose. Likewise, the controller may increase the overpressure and/or negative pressure in all air chambers if an extension of the manipulator increases, and/or reduce the overpressure or negative pressure in all air chambers of the air chamber arrangement if an extension of the manipulator decreases, or may be equipped for this purpose.

An extension is presently understood in particular as a distance of a center of gravity or a center of mass of the manipulator from a, preferably statically stable, in particular tilt-free reference. Likewise, an extension may also designate, for example, a horizontal distance between a tool center point (TCP) and a base of the manipulator. The extension may be determined from the pose of the manipulator. Correspondingly, in one embodiment, the carrier system comprises a detection means for detecting a pose of the manipulator; the detecting means is connected to the controller by signals, for example, joint sensors or the like.

A tilting moment of the carrier system about the horizontal depends in particular on a working load of a manipulator secured on the carrier: if the manipulator has a larger working load, then this may induce a larger tilting moment. Therefore, in one embodiment the controller regulates the supply of the air chamber arrangement with compressed air and/or negative pressure based on a load capacity of the manipulator secured on the carrier system, or is equipped for this purpose. In one embodiment, the controller increases an overpressure or negative pressure in one or more air chambers of the air chamber arrangement if a working load of the manipulator increases, and/or reduces an overpressure or negative pressure in one or more of the air chambers of the air chamber arrangement if a working load of the manipulator decreases, or is equipped for this purpose.

A working load is presently understood to be a useful load, secured in particular on a manipulator, preferably detachably. The working load may, for example, be determined from drive forces of the manipulator. Correspondingly, in one embodiment the carrier system has a detection means for detecting a working load of the manipulator; the detecting means is connected to the controller by signals, for example, joint sensors or the like.

A tilting moment of the carrier system about the horizontal influences, in particular, a pose of the carrier: a larger tilting moment causes a stronger deflection of the carrier with respect to the horizontal. Therefore, in one embodiment, the controller regulates the supply of the air chamber arrangement with compressed air and/or negative pressure based on a position and orientation of the carrier, or is equipped for this purpose. In one embodiment, the controller increases an overpressure or negative pressure in one or more of the air chambers of the air chamber arrangement if a deflection of the carrier with respect to the horizontal increases, and/or reduces an overpressure or negative pressure in one or more of the air chambers of the air chamber arrangement if a deflection of the carrier with respect to the horizontal decreases, or is equipped for this purpose. In one embodiment, the controller increases an overpressure in one or more air chambers on one side of the carrier toward which the carrier leans, and/or increases a negative pressure in one or more air chambers on one side from which the carrier leans away, or is equipped for this purpose. Likewise, the controller may increase the overpressure and/or negative pressure in all air chambers if a deflection of the carrier with respect to the horizontal increases, and/or reduce the overpressure or negative pressure in all air chambers of the air chamber arrangement if a deflection of the carrier with respect to the horizontal decreases, or may be equipped for this purpose.

Correspondingly, in one embodiment, the carrier system comprises a detection means for detecting a position and orientation, in particular a deflection, of the carrier with respect to the horizontal; the detecting means is connected to the controller by signals, for example, one or more distance sensors spaced apart from one another for detecting a vertical floor distance of the carrier, angular position sensors, or the like.

A tilting moment of the carrier system about the horizontal and an air pressure in the air chamber arrangement depend reciprocally upon one another: thus, a tilting moment may increase the overpressure in air chambers which counteract this, and/or reduce a negative pressure in air chambers, which counteract the tilting moment by increasing a floor gap. Conversely, a reduction of an overpressure or an increase of a negative pressure in air chambers causes a tilting moment to the side of these chambers. Therefore, in one embodiment, the controller regulates the supply of the air chamber arrangement with compressed air and/or negative pressure based on an air pressure in the air chamber arrangement, or is equipped for this purpose. In one embodiment, the controller increases an air supply to one or more air chambers of the air chamber arrangement if an overpressure in one or more of the air chambers of the air chamber arrangement decreases, increases an air discharge out of one of more of the air chambers of the air chamber arrangement if a negative pressure in one or more of the air chambers of the air chamber arrangement decreases, reduces an air supply to one or more of the air chambers of the air chamber arrangement if an overpressure in one or more of the air chambers of the air chamber arrangement increases, and/or reduces an air discharge from one of more of the air chambers of the air chamber arrangement if a negative pressure in one or more of the air chambers of the air chamber arrangement increases, or is equipped for this purpose.

Correspondingly, in one embodiment the carrier system has a detecting means for detecting an air pressure in the air chamber arrangement, which is connected to the controller by signals, for example, pressure sensors or the like.

According to one aspect of the present invention, a positioning device for a robot, in particular a surgical robot, or a positioning device for robot arrangement, in particular a surgical robot arrangement with a robot, in particular a surgical robot, has a (positioning device) base and a (positioning device) flange, on which the robot, in particular the surgical robot, is securable or is secured, in particular detachably, for example, electromagnetically, hydraulically, and/or by using screws.

In one embodiment, the robot has an end effector, in particular a surgical end effector, which in one refinement is provided or equipped for mechanical, optical, and/or fluidic functions, in particular on or in a patient, in particular for compressing, in particular for clamping, separating, in particular cutting or inserting, drilling, transmitting and/or receiving of electromagnetic radiation, in particular of visible light, and/or inflow and/or discharge of liquids and/or gases. In one embodiment, the end effector is detachably securable or is detachably secured, for example electromagnetically, hydraulically and/or by screwing, latching, or clamping, on a robot flange of the robot, in particular via an instrument shaft. In one embodiment, the instrument shaft is inserted into a natural or artificial bodily opening, or is provided or equipped for this purpose; in one refinement, the extent of the bodily opening is at most twice a maximum extent of the end effector and/or at most 15 cm. Thus, in one embodiment, the surgical robot is provided or equipped for minimally invasive surgery.

In one embodiment, the robot comprises six, in particular at least seven joints, in particular rotary joints moveable, in particular by electromotor drives of the robot, which joints connect the end effector or robot flange to a robot base which is securable or is secured on the positioning device flange.

The positioning device flange is connected to the positioning device base by a kinematic system which has at least two joints, in particular rotary joints. The positioning device flange is adjustable or is adjusted, in particular translationally from a first, in particular Cartesian position relative to the positioning device base, in particular, at least substantially on a circular path or straight line, into a second, in particular Cartesian position relative to the base by means of the kinematic system, the second position being spaced apart from the first position. The joints of the kinematic system are connected to one another by rigid links, preferably rigid links, in particular arms, like rods, bars, bowls, or the like, which are correspondingly designated as links of the kinematic system. These are designated, together with the positioning device flange and the positioning device base, jointly as links of the positioning device.

In one embodiment, the positioning device flange is adjusted prior to a surgical operation, in particular prior to an (initial) interaction of the end effector with the patient, or is equipped or provided for this purpose, which is presently designated as prepositioning of the robot base (prior to the operation by the robot). Additionally or alternatively, the positioning device flange is adjusted during the surgical operation, in particular during a standstill of the end effector at or in the patient, or is equipped or provided for this purpose, which is presently designated as a repositioning of the robot base (during the operation by the robot). Correspondingly, the present invention relates in particular to a prepositioning and/or repositioning of the robot.

In one embodiment, the robot base is connectable or is connected rigidly or immovably to the positioning device flange. In another embodiment, the robot base is connectable or is connected to the positioning device flange, to be linearly moveable in particular by a linear axis in addition to the kinematic system or an additional linear joint in addition to the joints of the kinematic system. Thus, in particular, a radius of a circular arc, on which the positioning device flange is guided by the kinematic system and the orientation means, may be varied, or a straight line, along which the positioning device flange is guided by the kinematic system and the orientation means, may be displaced in parallel. Preferably, this additional linear axis is fixable and/or is parallel or perpendicular to a first or base axis of rotation of the robot connected to the positioning device flange. Additionally or alternatively, in one embodiment, the robot base is rotatably connectable or connected to the positioning device flange, in particular by another rotary joint in addition to the joints of the kinematic system. Thus, in particular, an orientation of the robot base may be varied relative to the positioning device flange. Preferably, this additional rotary joint is fixable, and/or the axis of rotation thereof is parallel or perpendicular to a first or base axis of rotation of the robot connected to the positioning device flange.

According to one aspect of the present invention, the positioning device has an orientation means which reorients the positioning device flange as a result of or as a function of, in particular a manual or actuated, adjustment of the positioning device flange from the first position into the second position, from a first orientation, in particular angular orientation, in the first position into a second orientation, in particular angular orientation, in the second position, or is equipped or provided for this purpose, which in one refinement is rotated about a reference axis, in particular a horizontal, by at least 75 degrees, in particular at least 85 degrees, preferably more than 90 degrees relative to the first orientation.

Thus, in one embodiment, the robot or the base thereof may be positioned, in particular arranged selectively on a wall or ceiling or floor in an easy and/or reliable way, in particular by medical personnel without corresponding kinematic knowledge, in particular a first or base axis of rotation of the robot is selectively at least substantially horizontal or vertical.

The orientation means, which effects this reorientation as a result of the adjustment, in particular, at or during the adjustment from the first position into the second position, advantageously reduced for the user the number of degrees of freedom which he/she must set: he/she must merely adjust, in particular pull or push, the positioning device flange or the robot base connected thereto into the first position or second position, in particular translationally, and the orientation means thereby automatically effects a corresponding reorientation, in particular a rotation, of the positioning device flange or the robot base connected thereto from the first orientation into the second orientation. Conversely, in one embodiment, the orientation means may also effect an adjustment from the first position into the second position as a result of a reorientation from the first orientation into the second orientation. In one embodiment, the orientation may thereby be changed between an at least substantially horizontal orientation and a vertical orientation, due to the preferred angle range of at least 75 degrees, in particular at least 85 degrees, preferably more than 90 degrees.

In one embodiment, the positioning device flange is adjusted or is adjustable, by means of the kinematic system, into one or more intermediate positions between the first and second position relative to the positioning device base, wherein the orientation means of the flange reorients the flange, as a result of an adjustment from the first or second position into such an intermediate position, into an intermediate orientation in the intermediate position, or is equipped or provided for this purpose; in one refinement, the intermediate orientation is rotated about the reference axis by at least 25 degrees and/or at most 60 degrees with respect to the first and/or the second orientation.

Thus, in one embodiment, the robot or its base may also be selectively arranged in the same way in one or more intermediate positions and orientations between a wall, and a ceiling or floor mounted position and orientation, in particular, a first or base axis of rotation of the robot may be tilted with respect to the horizontal and vertical.

In one embodiment, the positioning device flange is maximally adjustable between the first and second position, which thus define or delimit a maximum adjustment path of the positioning device flange. In one alternative embodiment, the positioning device flange is, in contrast, adjustable beyond the first and/or second position, so that the first and second position define or specify a minimum adjustment path of the positioning device flange.

In one embodiment, the kinematic system or the positioning device flange is fixable in at least the first and/or the second position, preferably also in one or more intermediate positions, particularly in discrete, predefined intermediate positions or steplessly in any intermediate position between the first and second position.

In one embodiment, the kinematic system comprises at least one rotary joint, in particular at least three rotary joints, in particular arranged in series, in particular with parallel axes of rotation. Additionally or alternatively to one or more rotary joints, in one embodiment the kinematic system has at least one linear joint or one linear axis.

In one embodiment, an advantageous working space for the kinematic system and/or a structurally advantageous kinematic system is provided by one or more rotary joints, in particular in combination with one or more linear axes.

In one embodiment, the kinematic system comprises three rotary joints with parallel axes of rotation, the rotary joints arranged in series, or connected in pairs by links, in particular rigid links, of the kinematic system. As subsequently described in greater detail, thus, two parallelograms, in particular, or one four-bar guide mechanism may be represented using the three rotary joints of the kinematic system and a virtual point of rotation which is stationary with respect to the positioning device base; this four-bar guide mechanism constantly aligns the positioning device flange to the virtual point of rotation.

In another embodiment, the kinematic system comprises a rotary joint and a linear joint or a linear axis, which are connected by a link, in particular a rigid link, of the kinematic system in one refinement. As likewise is subsequently described in greater detail, a boom guide may thus be represented, which guides the positioning device flange approximately in a straight line; however, it may be advantageous, in particular structurally advantageous, with respect to a four-bar guide mechanism.

In one embodiment, the orientation means comprises, or is thus implemented to be, a corresponding controller which is equipped, in particular, with software or programming, and actuators commanded by this controller, which is provided or equipped for the purpose of moving joints, in particular rotary joints and/or linear axes, of the kinematic system using correspondingly controlled actuators, in particular electromotors, in such a way that the positioning device flange is reoriented from the first orientation into the second orientation, as a result of an adjustment of the positioning device flange from the first position into the second position, or is reoriented into an intermediate orientation as a result of an adjustment into the corresponding intermediate position. In one embodiment, an adjustment of the positioning device flange may be carried out manually and is detected by corresponding joint sensors of the kinematic system and is transmitted to the controller, which controls the actuators on the basis of the detected adjustment in order to effect the corresponding reorientation. Likewise, in one embodiment, an adjustment of the positioning device flange may be carried out by the controller, which thereby controls the actuators so that a corresponding reorientation is thereby also effected.

Thus, a particularly flexible orientation means may be provided in one embodiment.

In another embodiment, the orientation means is mechanically implemented or designed. Thus, in one embodiment, a particularly simple, reliable, and/or power-supply-independent orientation means may be provided, which automatically reorients the positioning device flange into the second orientation or into an intermediate orientation, in particular during a manual adjustment into the second position or into an intermediate position.

Correspondingly, in one embodiment, the orientation means comprises one or more mechanical positive couplings or positive guides made from in each case two links of the positioning device; the links are connected in each case by one or more, in particular at least two, joints of the kinematic system, in particular one mechanical positive coupling of the positioning device flange is connected to one link of the kinematic system and/or one mechanical positive coupling of the positioning device base is connected to one (other) link of the kinematic system or one mechanical positive coupling of the positioning device base is connected to the positioning device flange.

A mechanical positive coupling or positive guide in the meaning of the present invention mechanically reduces, in particular reduces in a positive-locking or friction-locking manner, the kinematic degree of freedom of the links connected by the joint(s), to at least one, in particular to zero; i.e., the one link couples unambiguously or automatically to the other link of the positioning device, which is connected to the one link by the joint(s), so that an orientation of the one link automatically determines the orientation of the other link.

Correspondingly, in one embodiment, a mechanical positive coupling may comprise, in particular may be, a single or multistage transmission, in particular a gear train, traction gear, worm gear, cam gear, coupling gear, in particular a connecting rod transmission, piston rod transmission, coupling rod transmission, or a hydraulic or fluidic transmission. In one refinement, a transmission ratio equals one, so that an orientation change of the one link is realized identically or in equal dimensions into an orientation change of the other link.

In one embodiment, one or more mechanical positive couplings are detachable or detached, in particular detached manually and/or are actuated, in particular pneumatically, hydraulically, electromotorically, and/or electromagnetically, for example, by decoupling a transmission or the like. Thus, in one embodiment, the kinematic system may be compactly folded when not required.

In one embodiment, the positioning device base and the positioning device flange are connected to parallel axes of rotation by three rotary joints, arranged in series, wherein a four-bar guide mechanism, in particular a parallelogram guide arrangement, is formed, in particular mechanically, by the orientation means: the guide mechanism comprises the rotary joints, arranged in series, of the kinematic system and one virtual point of rotation, which is stationary relative to the positioning device base, with parallel axes or rotation. Due to such a four-bar guide mechanism, in a particular parallelogram guide, the positioning device flange remains constantly aligned at the virtual point of rotation during a translational adjustment on a circular arc path.

In one refinement, the kinematic system comprises a first rotary joint which connects the positioning device base to a first link of the kinematic system, a second rotary joint which connects the first link to a second link of the kinematic system, and a third rotary joint which connects the second link of the kinematic system to the positioning device flange, and the orientation means comprise a mechanical positive coupling of the positioning device base to this second link of the kinematic system and one additional positive coupling of the positioning device flange to this first link of the kinematic system.

In another embodiment, the positioning device base and the positioning device flange are connected by a linear joint or a linear axis and a rotary joint connected thereto, wherein a mechanical boom guide or boom arm guide, formed by the orientation means, aligns the positioning device flange approximately at a virtual point of rotation during a translational adjustment on a straight line, or maintains a reference point within a delimited circle which is fixed with respect to the positioning device flange.

In one refinement, the kinematic system comprises a linear joint which connects the positioning device base to a first link of the kinematic system, and a rotary joint which connects the first link of the kinematic system to the positioning device flange, and the orientation means comprises a mechanical positive coupling of the positioning device base to the positioning device flange. In one embodiment, the linear joint is rotatably connected to the positioning device base. Thus, an inclination of the straight line, along which the positioning device flange is adjustable, may be advantageously varied relative to the positioning device base, in particular in order to also bring the positioning device into a compact transport and/or storage position.

In one embodiment, at least one or more joints, in particular all joints, of the kinematic system have a latch for locking or fixing the respective joint. Due to a selective locking of one or more joints, the number of degrees of freedom of the kinematic system may be reduced, in particular to zero, by locking all joints of the kinematic system, or the kinematic system, and thus the positioning device flange, are fixed relative to the positioning device base, in particular, in the first position, the second position, or at least one intermediate position, preferably in any intermediate position between the first and second position, which are specified in one embodiment by the maximum displacement or adjustment paths of the kinematic system.

According to one aspect of the present invention, the orientation means reduces the number of the degrees of freedom of the positioning device between the positioning device base and the positioning device flange, which are defined by the degrees of freedom of the joints of the kinematic system, by at least one, preferably to one.

Correspondingly, the locking of a joint would already eliminate this remaining degree of freedom and would fix the positioning device flange in the corresponding position and orientation relative to the positioning device base. Due to the additional locking of additional joints, in particular all joints, of the kinematic system in one embodiment, the orientation means, in particular one or more mechanical positive couplings, may be unloaded. Additionally or alternatively, such a locking may advantageously redundantly fix the positioning device flange. In particular, due to such a redundant fixing, the orientation means, in particular one or more mechanical positive couplings, in particular transmissions, may have greater tolerances and/or flexibilities, as the robot may compensate for this, in particular after a calibration in which the position and orientation of the robot base is precisely fixed by the locked joints.

In one embodiment, the joints are mechanically locked or lockable, in particular in a positive-locking or friction-locking manner, for example, by closing latches, setting parking brakes, or the like.

In one embodiment, the joints are manually locked or lockable. This facilitates, in particular, the direct handling of the positioning device. Additionally or alternatively, in one embodiment, the joints are actuated to be locked or lockable, for example, by electromagnetic closing or venting of brakes, latches, or the like. This facilitates, in particular, the locking of joints that are difficult to access.

In one embodiment, one or more joints are locked or lockable together with at least one different joint of the kinematic system, in particular all joints of the kinematic system are locked or lockable together. Thus, a desired position may be directly redundantly fixed and the orientation means unloaded. Alternatively or additionally, in one embodiment, in particular in another operating mode, one or more joints are locked or lockable independently from at least one different joint of the kinematic system. Thus, in one embodiment, the position and orientation of the positioning device flange may be fixed in interaction with the orientation means, as previously described. The different joint(s) may be advantageously moved further, if the orientation means is ineffective, for example by loosening one or more mechanical positive couplings or the like.

In one embodiment, the positioning device comprises at least one biasing means, in particular a mechanical and/or pneumatic biasing means, which binds together two links of the positioning device connected to one another by at least one joint of the kinematic system, and which is more strongly biased by a movement of the positioning device into a position and orientation in which the positioning device has a lower position and orientation energy, in particular by adjusting the positioning device flange from a raised position into a lowered position. Thus, an at least partial weight compensation is advantageously provided which facilitates an adjustment of the positioning device flange, in that energy is transferred between position and orientation energy and energy stored in the biasing means. In other words, in one embodiment, the biasing means is more strongly biased in that respective position of the first and second position of the positioning device flange, in which the positioning device has the lower position and orientation energy, than in the other of the first and second positions of the positioning device flange, in which the positioning device has, in contrast, the greater position and orientation energy.

In one embodiment, the positioning device comprises at least two links which are connected to one another by at least one joint of the kinematic system and may be folded together into a storage position, in which these two links are at least substantially parallel to one another in opposite directions. Thus, the positioning device may be advantageously compactly stored when not in use.

In one embodiment, the positioning device has a carrier on which the positioning device base is mounted to be linearly moveably in one or multiple axes and/or rotatable. Thus, in one embodiment, the positioning device base may be prepositioned with respect to the carrier. This advantageously facilitates a better adjustment of the positioning device to different operating theaters or operating areas with correspondingly different patient orientations and patient accesses, and, in addition to the previously described change between a wall and a ceiling or floor mounting, or a horizontal or vertically hanging or standing orientation of the first or base axis of the robot, prevents, in particular, interference between multiple mutually acting robots.

In one embodiment, the carrier is stationarily fixed, permanently or detachably, in particular on a wall, ceiling, or floor of the operating theater. In another embodiment, the carrier is moveable or mobile, in particular manually, in particular by the air chamber arrangement described here, by a corresponding mechanism, in particular a travelling mechanism without a motor, or the like. Likewise, the carrier may also be automobile, for example due to a corresponding travelling mechanism, in particular a motor driven mechanism, or the like.

In one embodiment, the positioning device base is rotatable about a vertical and/or horizontal axis in an operating position of the carrier. This facilitates, in particular, an advantageous alignment relative to the surroundings. Additionally or alternatively, the positioning device base is rotatable about one axis which is perpendicular or parallel to an axis of the joint of the kinematic system to which the positioning device base is connected. This facilitates, in particular, an advantageous alignment of the robots among one another.

Additionally or alternatively, the positioning device base is linearly moveable, vertically and/or horizontally, in an operating position of the carrier. This facilitates, in particular, an advantageous alignment relative to the surroundings. Additionally or alternatively, the position device base is linearly moveable in or along one axis which is perpendicular or parallel to an axis of the joint of the kinematic system to which the positioning device base is connected. This facilitates, in particular, an advantageous alignment of the robots among one another.

In one embodiment, the positioning device base is fixable on the carrier in one or more positions and/or orientations so that the robot base secured on the positioning device flange may be fixed with respect to the surroundings via the positioning device and the carrier.

If one robot arrangement in one embodiment comprises at least two of the positioning devices described here, to which positioning device flanges respectively one of the robots described here is securable or secured, then in one refinement, the positioning device bases of at least two of the positioning devices may be mounted on the carrier to be jointly linearly moveable in one or more axes in the way described here and/or rotatable. Likewise, in another refinement, the positioning device bases of at least two of the positioning devices may be mounted to be independently linearly moveable in one or more axes in the way described here and/or rotatable.

In one embodiment, the carrier has a housing in which the positioning device base, the kinematic system, in particular folded for this purpose, and/or the positioning device flange may be completely or partially retracted. Thus, in one embodiment, a compact storage and/or transport position is provided, in which the areas of the positioning device retracted into the housing and the surroundings, in particular operating personnel, are mutually protected.

In one aspect of the present invention, one robot arrangement comprises one positioning device described here and one robot described here, the base of the robot arrangement or of the robot being securable or secured, in particularly detachably, to the positioning device flange.

According to another aspect of the present invention, to position a robot of a robot arrangement described here with a positioning device, which comprises a base and a flange to which the robot is secured, wherein the flange is connected to the base by a kinematic system, by means of which the flange is adjustable from a first position relative to the base into a second position relative to the base, the second position being spaced apart from the first position, and/or is reorientable from a first orientation relative to a reference axis into a second orientation relative to the reference axis, the second orientation being rotated with respect to the first orientation, in particular with a positioning device according to another of the aspects described here, the robot is controlled for adjustment and/or reorientation, in particular manual adjustment and/or reorientation of the positioning device flange into a predefined positioning pose, in particular by corresponding actuation of its joint drives.

Thus, the prepositioning and/or repositioning of the robot may be advantageously facilitated.

In one embodiment, the predefined positioning pose is a pose in which the robot has an advantageous manipulability or movability, in particular one or more joints of the robot are respectively moveable in opposite directions, at least substantially in equal magnitudes. Thus, for example, one rotary joint, which has an angle range of 180 degrees, has an angle setting of approximately 90 degrees in the predefined positioning pose. Additionally or alternatively, in particular in the case of joints with unlimited mobility, a predefined positioning pose, in which the robot has an advantageous manipulability or movability, may be characterized, for example, by a large distance, in particular by a maximum distance to a singular pose of the robot or may be characterized in that the robot may execute preferred end effector movements, in particular statistically frequent end effector movements, by selected joints or joint combinations in the pose.

In one embodiment, the predefined positioning pose is selected from multiple predefined poses, for example, on the basis of an operation to be carried out and/or a position and orientation of the positioning device flange relative to the positioning device base and/or a position and orientation of the positioning device base relative to the carrier. Thus, the user may preposition the robot in a pose that is optimal for the respective application.

According to another aspect of the present invention, additionally or alternatively to controlling the robot into a predefined position pose for adjustment and/or reorientation, in particular, manual adjustment and/or reorientation of the positioning flange, and after fixing the positioning device, in particular fixing the positioning device flange in a position and orientation relative to the positioning device base and/or fixing the positioning device base relative to the surroundings, a calibration means, in particular a calibration means fixed on the positioning device base, positioning device carrier, or the surroundings, is driven into one or more different poses of the robot using a reference point fixed at the robot, in particular a designated point of the robot flange or of the robot end effector, and the associated joint coordinates of the robot are evaluated. In this way, a reference system for a controller of the robot may be calibrated and thus a prepositioning or a repositioning of the robot base may be compensated for.

As already explicitly emphasized, the robot(s) described here may be, in particular surgical robots with a surgical end effector. In the embodiments, surgical robots are therefore used, for which the present invention is particularly advantageous. Likewise, the manipulator(s) described here, in particular the robots, may also be industrial and/or service manipulators, in particular industrial and/or service robots, for which the present invention is likewise advantageous.

BRIEF DESCRIPTION OF THE DRAWINGS

Additional advantages and features arise from the subclaims and exemplary embodiments. In addition, the figures show the following, in part schematically.

DETAILED DESCRIPTION

Figure 7:
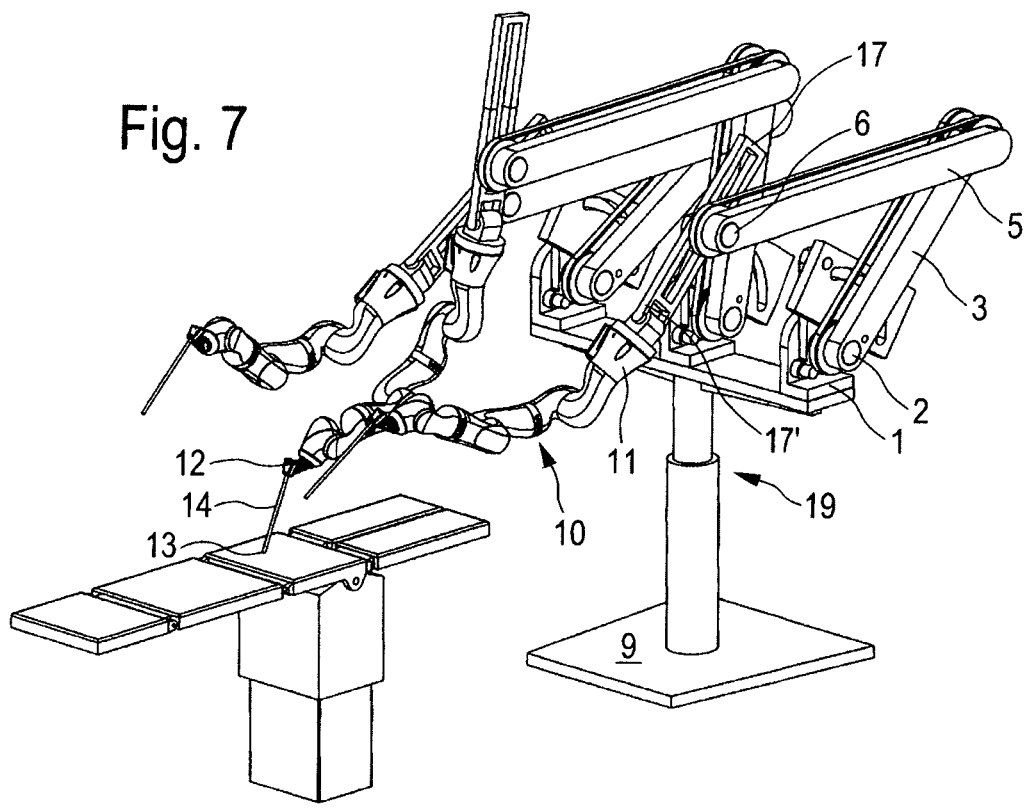
FIG. 7: shows a surgical robot arrangement according to one embodiment of the present invention in a perspective view.

FIG. 7 shows a surgical robot arrangement according to one embodiment of the present invention in a perspective view. This comprises a carrier 9, to which the three positioning devices are mounted to be jointly linearly moveable on one axis and rotatable, to which positioning devices a surgical robot is in turn respectively secured. The positioning devices and surgical robots are each structurally identical so that only the front surgical robot or positioning device in FIG. 7 will be subsequently described in greater detail as representative.

This positioning device has a positioning device base 1 and a positioning device flange (7) (compare FIG. 1) to which the seven-axis surgical robot 10 is secured.

Figure 1:
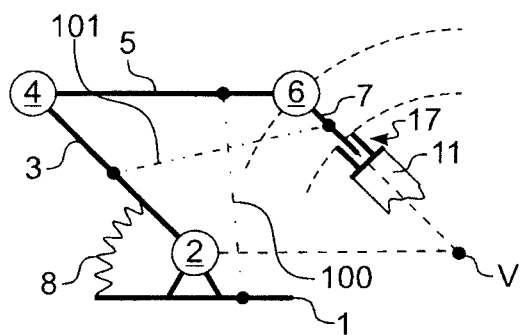
FIG. 1: shows a positioning device according to one embodiment of the present invention with an orientation means.

Surgical robot 10 is provided for minimally invasive surgery and comprises for this purpose a surgical end effector 13 which is secured via an instrument shaft 14 to a surgical robot flange 12 of the surgical robot which in turn is connected by seven rotary joints to a surgical robot base 11 which is secured to positioning flange 7 (compare FIG. 1).

As is evident, in particular in FIG. 1, in which a positioning device is represented schematically, which corresponds to the positioning device from FIG. 7, except for subsequently described differences, positioning device flange 7 is connected to positioning device base 1 by a kinematic system which comprises three joints 2, 4, 6.

The positioning device flange may be translationally adjusted from a first Cartesian position relative to the positioning device base on a circular path, indicated by a dashed line in FIG. 1, to a second position, which is spaced apart from the first position. The joints of the kinematic system are connected to one another by rigid links 3, 5.

In the embodiment from FIGS. 1, 7, in order to be linearly movable, surgical robot base 11 is connected to positioning device flange 7 by an additional linear joint 17 which is fixable to the rotary joints 2, 4, 6 of the kinematic system. This is not shown in the embodiments of FIGS. 2, 3, and 5 for better clarity.

In the embodiment from FIG. 7, surgical robot base 11 is additionally rotatably secured to positioning flange 7 or to the drive of linear joint 17 by an additional rotary joint 17', which is additionally fixable to joints 2, 4, 6 of the kinematic system. The axis of rotation of additional rotary joint 17' is perpendicular to a first or to the base axis of rotation of surgical robot 10.

Figure 6:
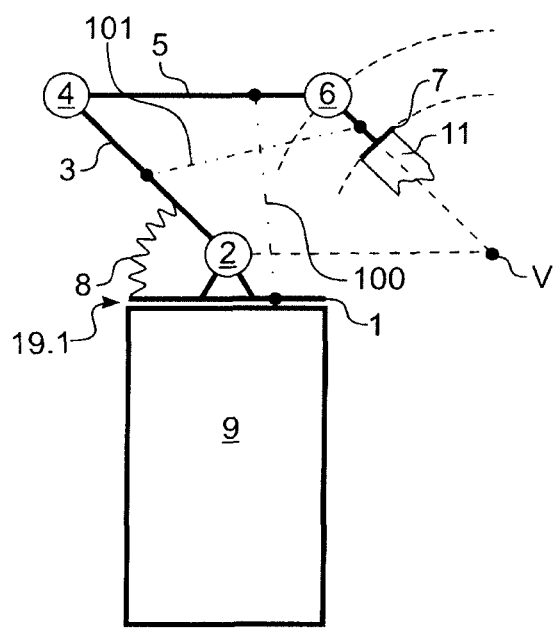
FIG. 6: shows a positioning device according to another embodiment of the present invention.

In the embodiment from FIG. 6, which generally matches the embodiment from FIG. 1, surgical robot base 11 is, in contrast, rigidly connected to positioning device flange 7. Therefore, positioning device base 1 is secured to a carrier 9 to be horizontally movable through a linear axis 19.1, which is subsequently described in greater detail with reference to FIG. 9.

As these embodiments show, surgical robot base 11 may be connected to positioning device flange 7 rigidly (compare FIG. 6), to be linearly moveable (compare FIG. 1), and/or rotatably (compare FIG. 7).

Figure 2:
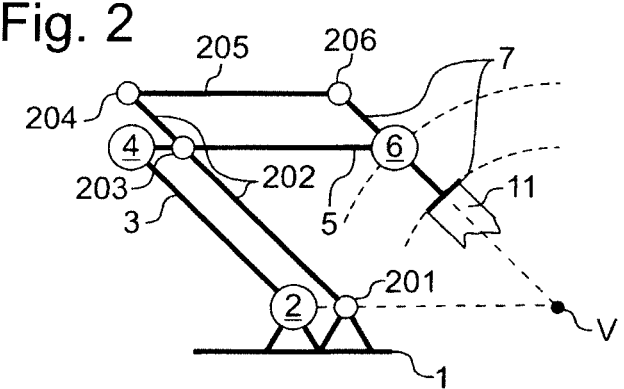
FIG. 2: shows the positioning device from FIG. 1, wherein the orientation means comprises two coupling rods.
Figure 3:
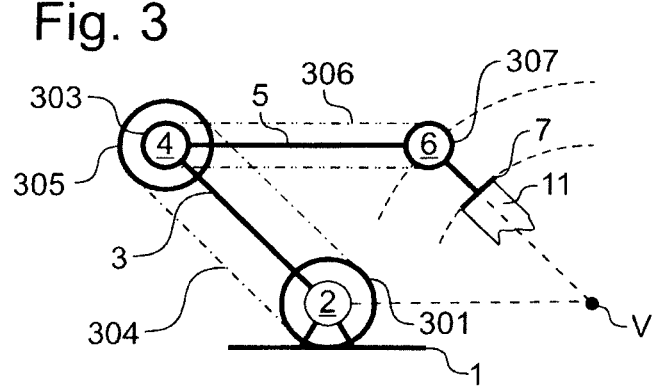
FIG. 3: shows the positioning device from FIG. 1, wherein the orientation means comprises two traction drives.

As now is described in greater detail, in particular with reference to FIGS. 1 through 3, the positioning device has an orientation means, which reorients positioning device flange 7 from a first orientation in the first position into a second orientation in the second position, the second position being rotated about a horizontal by 90 degrees relative to the first orientation, as a result of an adjustment of the positioning device flange from the first position into the second position.

Thus, in one embodiment, surgical robot 10 or base 11 thereof may be arranged selectively on a wall or ceiling in a simple and reliable way, and by medical personnel without corresponding kinematic knowledge. The orientation means thereby reduces the number of degrees of freedom which the user must set, so that this user need only adjust, in particular pull or push positioning flange 7 or surgical robot base 11 connected thereto into the first or second position, while the orientation means thereby automatically effects a corresponding reorientation of positioning device flange 7 or surgical robot base 11 connected thereto from the first orientation into the second orientation. This is indicated in FIG. 1 by a virtual point of rotation V at which positioning device flange 7 is aligned during an adjustment on the circular arc.

In the embodiments shown here, the orientation means is designed or implemented in each case mechanically, wherein joints 2, 4, 6 are passive or without actuators. In a modification (not shown) the orientation means may be likewise implemented by a controller and actuators commanded by the same, which thus move these joints, which in the modification are actuated, by the correspondingly controlled actuators, in particular electromotors, as this is subsequently described for the mechanically designed orientation means.

In the embodiment from FIG. 1 and correspondingly in FIGS. 6 and 7, the orientation means has a mechanical positive coupling 100 of positioning device base 1 with link 5 of the kinematic system, which is shown schematically in FIG. 1 by double-dashed-dotted lines, and another mechanical positive coupling 101 of positioning device flange 7 with link 3 of the kinematic system, which is shown schematically in FIG. 1 by dashed-dotted lines.

These mechanical positive couplings may comprise in particular a single or multistage gear train, traction gear, worm gear, cam gear, coupling gear, in particular a connecting rod transmission, piston rod transmission, coupling rod transmission, or a hydraulic or fluidic transmission.

To clarify, FIG. 2 shows in an exemplary way one embodiment of the positioning device from FIG. 1, in which the schematically-shown mechanical positive couplings 100, 101 are formed by coupling rod transmissions.

These comprise a rotary joint 201 fixed to the positioning device base, which rotatably mounts a first coupling rod 202 which in turn is rotatably mounted in a rotary joint 203 at link 5 of the kinematic system such that rotary joints 2, 4, 201, and 203 form a parallelogram guide with links 3 and 5 and also first coupling rod 202 and positioning device base 1. First coupling rod 202 is rotatably connected in a rotary joint 204 to a second coupling rod 205, which in turn is rotatably mounted in a rotary joint 206 at positioning device flange 7 such that rotary joints 6, 203, 204, and 206 form an additional parallelogram guide with link 5, first coupling rod 202, second coupling rod 205, and positioning device flange 7.

FIG. 3 shows for clarification in an exemplary way another embodiment of the positioning device from FIG. 1, in which the mechanical positive couplings 101, 101, shown there only schematically, are designed as traction gears.

These have a first synchronous disk 301 fixed to the positioning device base, the axis of first synchronous disk 301 aligning with the axis of joint 2, a second synchronous disk 305 rigidly connected to link 5, the axis of second synchronous disk 305 aligning with the axis of joint 4, and which is coupled via a first traction means 304 to first synchronous disk 301, a third synchronous disk 303 rigidly connected to link 3, the axis of third synchronous disk 303 likewise aligning with the axis of joint 4, and a fourth synchronous disk 307 rigidly connected to positioning flange 7, the axis of fourth synchronous disk 307 aligning with the axis of joint 6, and which is coupled to third synchronous disk 303 via a second traction means 306.

On the basis of the two exemplary embodiments of the mechanical positive guides 100, 101 using coupling rods or traction drives, it is clear that in each case a reorientation of positioning device flange 7 is thus effected as a result of an adjustment of positioning device flange 7 on the circular arc path indicated by the dashed line, which constantly aligns positioning device flange 7 at virtual point of rotation V. It is thereby clear to a person skilled in the art that mechanical positive guides 100, 101 may also be realized in other ways, instead of the embodiments shown. In particular, other coupling rod drives and traction drives may also be provided, for example, traction drives 303, 306, 307 for coupling link 3 and positioning flange 7 and coupling rod transmission 2, 3, 4, 5, 203, 202, 201, and 1 for coupling link 5 and positioning device base 1, wherein elements 203, 205, and 206 are then omitted.

In the embodiment from FIG. 1 and corresponding to FIGS. 2, 3, 6, and 7, positioning device base 1 and positioning device flange 7 are connected to parallel axes of rotation by three rotary joints arranged in series, wherein a mechanical parallelogram guide, formed by the orientation means, comprises the three rotary joints of the kinematic system arranged in series and virtual point of rotation V, which is stationary relative to positioning device base 1, with parallel axes of rotation. Correspondingly, the kinematic system comprises, with rotary joint 2, a first rotary joint which connects positioning device base 1 to (first) link 3 of the kinematic system, with rotary joint 4, a second rotary joint which connects (first) link 3 with (second) link 5 of the kinematic system, and with rotary joint 6, a third rotary joint which connects (second) link 5 of the kinematic system to positioning device flange 7; the orientation means comprises a mechanical positive coupling 100 of the positioning device base 1 to (second) link 5 of the kinematic system and another positive coupling 101 of positioning device flange 7 to (first) link 3 of the kinematic system.

Figure 5:
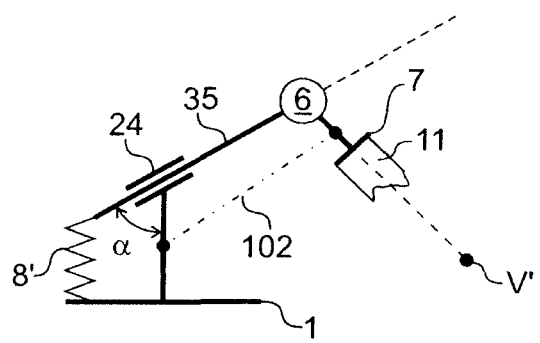
FIG. 5: shows a positioning device according to another embodiment of the present invention.

FIG. 5 shows in a way corresponding to FIG. 1 a positioning device according to another embodiment of the present invention, which may be used alternatively to the positioning device described with reference to FIGS. 1-3 and 6, in particular in the surgical robot arrangement from FIG. 7. In this embodiment, positioning device base 1 and positioning device flange 7 are connected by a linear joint or a linear axis 24 and a rotary joint 6 connected thereto, wherein a mechanical boom guide, formed by the orientation means, aligns the positioning device flange approximately at a virtual point of rotation V' during a translational adjustment on the dashed straight line in FIG. 5.

For this purpose, the kinematic system comprises linear joint 24, which connects positioning device base 1 to a first link 35 of the kinematic system, and a rotary joint 6, which connects first link 35 of the kinematic system to positioning device flange 7, wherein the orientation means comprises a mechanical positive coupling 102 of positioning device base 1 to positioning device flange 7, which is schematically shown in FIG. 5 by the double-dashed-dotted line corresponding to FIG. 1. In one modification (not shown), linear joint 24 is rotatably connected to positioning device base 1. Thus, an inclination or an angle $\alpha$ of the straight line, along which positioning device flange 7 is adjustable, may be advantageously varied relative to positioning device base 1.

In the embodiment described here, unactuated joints 2, 4, 6, or 24 of the kinematic system respectively comprise a locking mechanism for positive-locking or frictional-locking or fixing of the respective joint, for example, by closing the latches, setting parking brakes, or the like (not shown).

In the embodiment described here, the positioning devices each have a biasing means, indicated in FIGS. 1, 5, and 6 by a mechanical spring 8 or 8', which binds the two links 1, 3 connected to one another by joint 2 of the kinematic system or the two links 1, 35 connected to one another by joint 24 of the kinematic system, and is more strongly biased by a movement of the positioning device into a position and orientation in which it has a low position and orientation energy. Thus, an at least partial weight compensation is advantageously provided which facilitates an adjustment of the positioning device flange. In the remaining figures, biasing means are likewise preferably present, but are not shown for improved clarity.

In the embodiment from FIG. 7, the positioning device comprises, as described at the beginning, a carrier 9, on which the positioning device bases 1 of the three positioning devices are jointly mounted to be linearly moveable along a single axis and rotatable. In the embodiment from FIG. 7, carrier 9 is connected for this purpose by a lifting column 19 to a basic structure to which positioning device bases 1 are secured, wherein lifting column 19 is rotatable about its longitudinal axis.

Carrier 9 in the embodiment from FIG. 7 is stationary. In one modification, the carrier is mobile, in particular manually moveable.

In the embodiment from FIG. 7, positioning device bases 1 (in the case of a portable carrier in the operating position thereof) are rotatable, due to lifting column 19, about a vertical axis which is perpendicular to the axis of joint 2 of the kinematic system to which positioning device base 1 is connected. In addition, positioning device bases 1 are linearly moveable, due to lifting column 19, vertically along an axis which is perpendicular to the axis of joint 2 of the kinematic system to which positioning device base 1 is connected. The lifting column is lockable or fixable (not shown).

As previously stated, the surgical robot arrangement from FIG. 7 comprises three of the positioning devices described, in particular with reference to FIGS. 1-3, 5, and 6, whose positioning device bases are jointly mounted on carrier 9 to be linearly moveable and/or rotatable.

Figure 8:
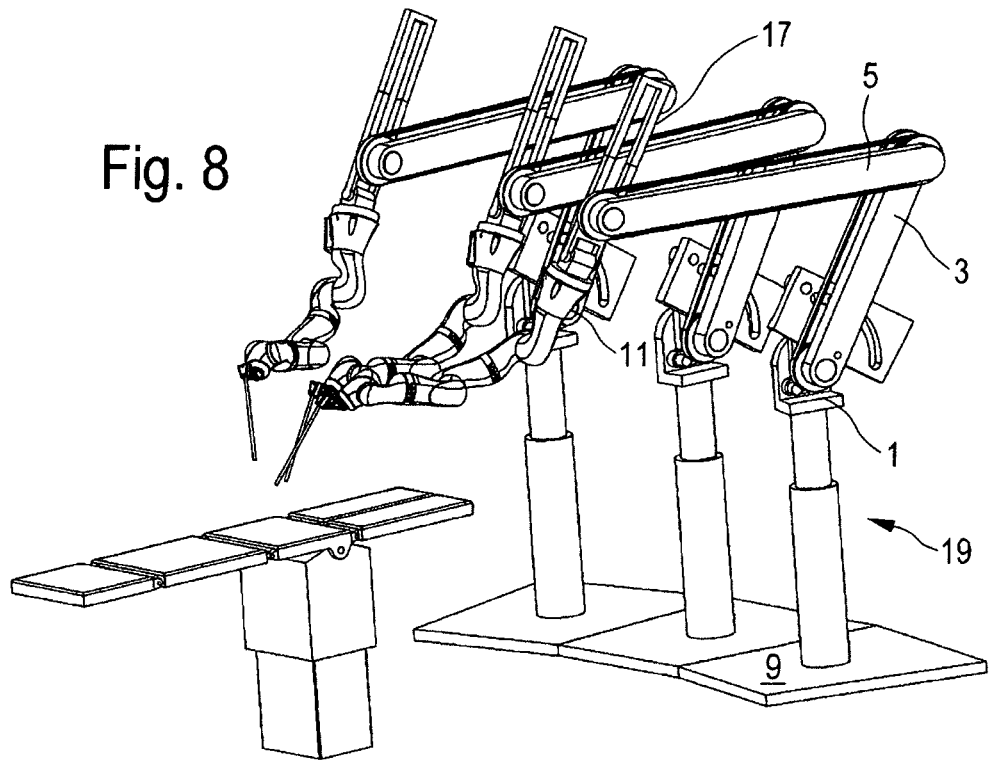
FIG. 8: shows a surgical robot arrangement according to another embodiment of the present invention in a perspective view.

FIG. 8 shows a surgical robot arrangement according to another embodiment of the present invention in a presentation corresponding to FIG. 7. Features corresponding with one another are designated with identical reference numerals so that subsequently only the differences with the embodiment from FIG. 7 are described and in general reference is made to that description.

In the embodiment from FIG. 8, positioning device bases 1 of the three positioning devices are mounted independently from one another in the previously described way using separate lifting columns 19 to be linearly moveably and rotatable on separate carriers 9.

Figure 9:
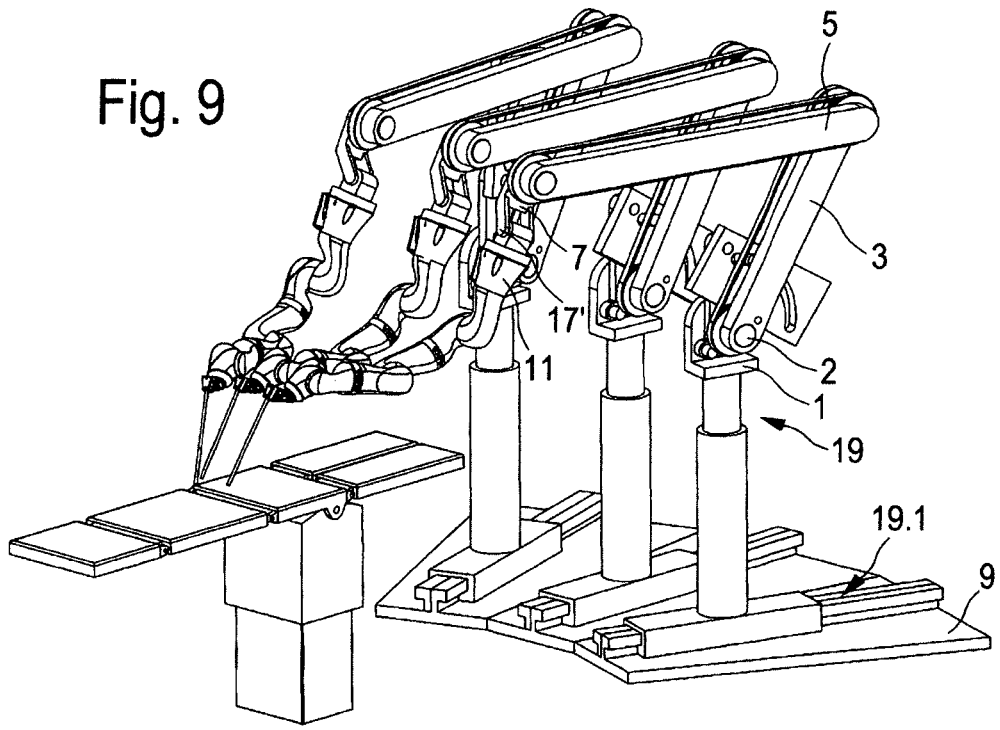
FIG. 9: shows a surgical robot arrangement according to another embodiment of the present invention in a perspective view.

FIG. 9 shows a surgical robot arrangement according to another embodiment of the present invention in a presentation corresponding to FIGS. 7, 8. Features corresponding with one another are designated with identical reference numerals so that subsequently only the differences with the embodiments from FIGS. 7, 8 are described and in general reference is made to those description.

In the embodiment from FIG. 9, separate lifting columns 19 are additionally linearly moveable in each case due to a horizontal linear axis 19.1, which is perpendicular to the axis of joint 2 of the kinematic system to which positioning device base 1 is connected. Therefore, in the embodiment from FIG. 9, additional linear axis 17, which links surgical robot base 11 directly to positioning device flange 7 via additional rotary joint 17', is omitted.

Figure 10:
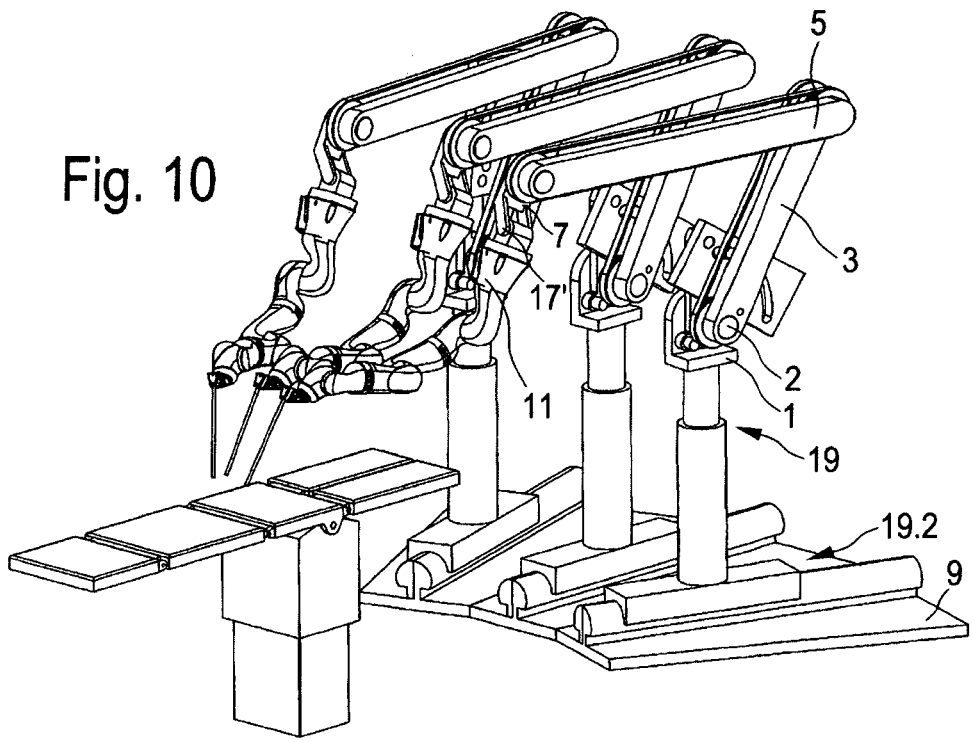
FIG. 10: shows a surgical robot arrangement according to another embodiment of the present invention in a perspective view.

FIG. 10 shows a surgical robot arrangement according to another embodiment of the present invention in a presentation corresponding to FIGS. 7, 8, 9. Features corresponding with one another are designated with identical reference numerals so that subsequently only the differences with the embodiment from FIG. 9 are described and in general reference is made to that description.

In the embodiment from FIG. 10, separate lifting columns 19 are in each case linearly moveable and also rotatable or tiltable due to a horizontal linear-rotary joint 19.2, whose axis is perpendicular to the axis of joint 2 of the kinematic system to which positioning device base 1 is connected.

With reference to the sequence of FIGS. 4A-4E, a storage procedure of a surgical robot arrangement according to one embodiment of the present invention or a surgical robot arrangement or a positioning device correspondingly designed for this purpose is described in greater detail. This surgical robot arrangement or positioning device may correspond in particular to one described above with reference to FIGS. 1-3, 5-10 so that reference is made to that description and subsequently only the differences are described.

In the embodiment from FIGS. 4A-4E, carrier 9 has a housing into which positioning device base 1, kinematic system 2-6, which is folded for this purpose, and positioning device flange 7 are retractable.

Figure 4A:
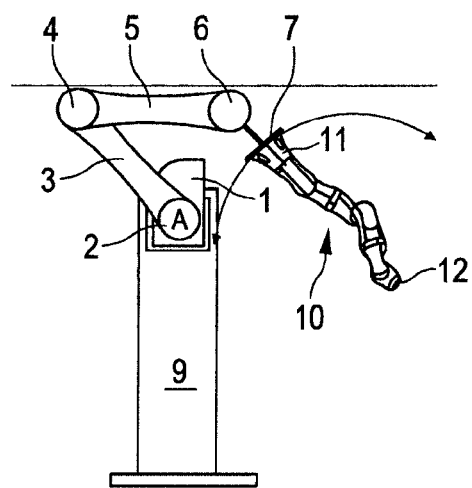
FIGS. 4A-4E: show a storage procedure of a surgical robot arrangement according to one embodiment of the present invention.
Figure 4B:
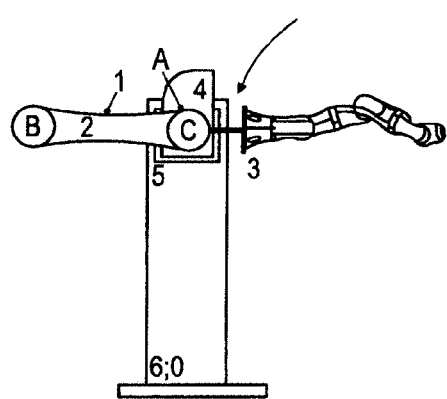
Figure 4C:
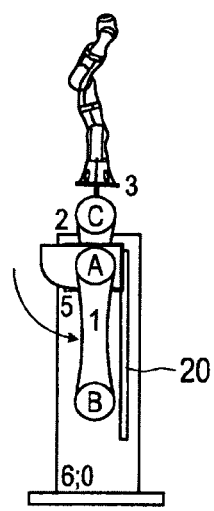
Figure 4D:
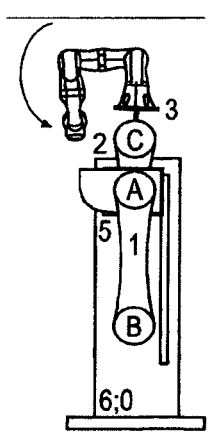
Figure 4E:
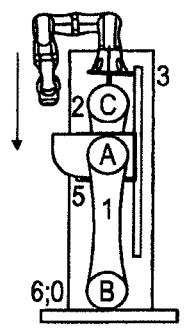

For this purpose, initially links 3, 5 of the kinematic system are folded together into a storage position in which these two links are parallel to one another in opposite directions (FIG. 4A→FIG. 4B). Subsequently, positioning device base 1, which is rotatably arranged on a slide 20 of carrier 9 for this purpose, is pivoted, by which means links 3, 5 pivot into the housing (FIG. 4B→FIG. 4C). Optionally, surgical robot 10 may be controlled into a compact storage pose (FIG. 4C→FIG. 4D). In another step, the positioning device is lowed into the housing by means of slide 20.

To position surgical robots 10 of the surgical robot arrangement according to FIGS. 7 through 10, the surgical robots are controlled by manual adjustment of positioning device flange 7 initially into a predefined positioning pose indicated in FIGS. 8 through 10, in which the surgical robots have an advantageous manipulability or movability. The positioning pose is selected from multiple predefined poses on the basis of an operation to be carried out.

After the positioning devices have been fixed in the manually set position and orientation, a calibration means, fixed on the positioning device base, positioning device carrier, or in the surroundings (not shown) is driven into multiple different poses of surgical robot 10 using a designated point of the surgical robot flange 12 or end effector 13, and the associated joint coordinates of the surgical robot are evaluated. In this way, a reference system of a controller of the surgical robot may be calibrated and thus a prepositioning or repositioning of its surgical robot base may be compensated for.

Figure 11:
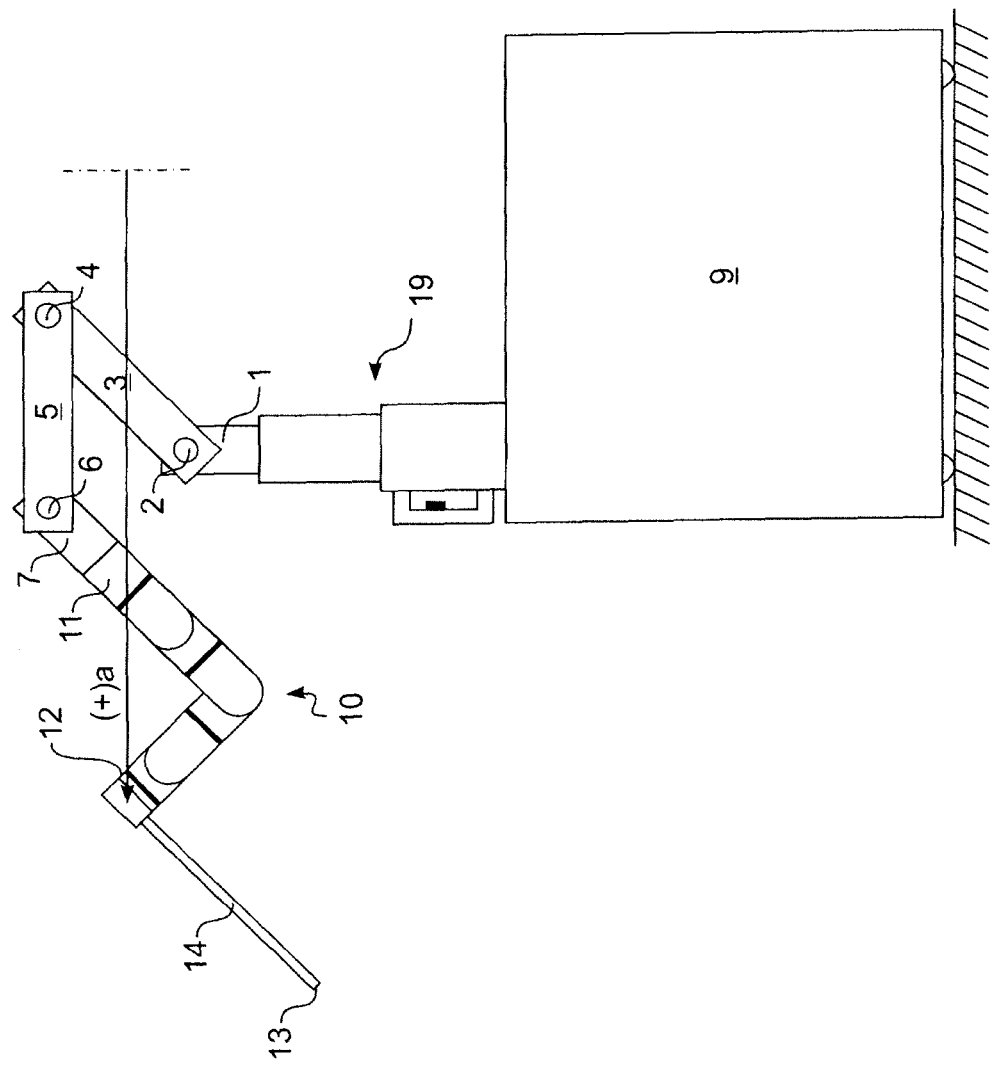
FIG. 11: shows a manipulator arrangement with a carrier system according to one embodiment of the present invention in a side view.

FIG. 11 shows a manipulator arrangement comprising a carrier system according to one embodiment of the present invention in a side view. Features matching the preceding embodiments are identified using identical reference numerals so that reference is made to that description. As already previously emphasized, reference is made again at this point that a positioning device, a manipulator arrangement, in particular a robot arrangement, a method for positioning a robot or a carrier system according to one aspect of the present invention is described using the example of surgical robots, wherein in a modification, other robots, in particular industrial robots or service robots may be likewise used at this point.

The already previously described, seven-axes surgical robot 10 is recognized, with instrument shaft 14 secured to robot flange 12 and surgical end effector 13. Surgical robot base 11 is secured to positioning device flange 7 of the positioning device, which is connected via kinematic system 2-6 to positioning device base 1, which is adjustably mounted on carrier 9 via lifting column 19. As already emphasized, a surgical robot arrangement represents an advantageous use of the carrier system subsequently explained with reference to FIGS. 11-14; however, this is not limited to the same: instead industrial manipulators or service manipulators, in particular industrial robots or service robots may likewise be used.

Figure 12:
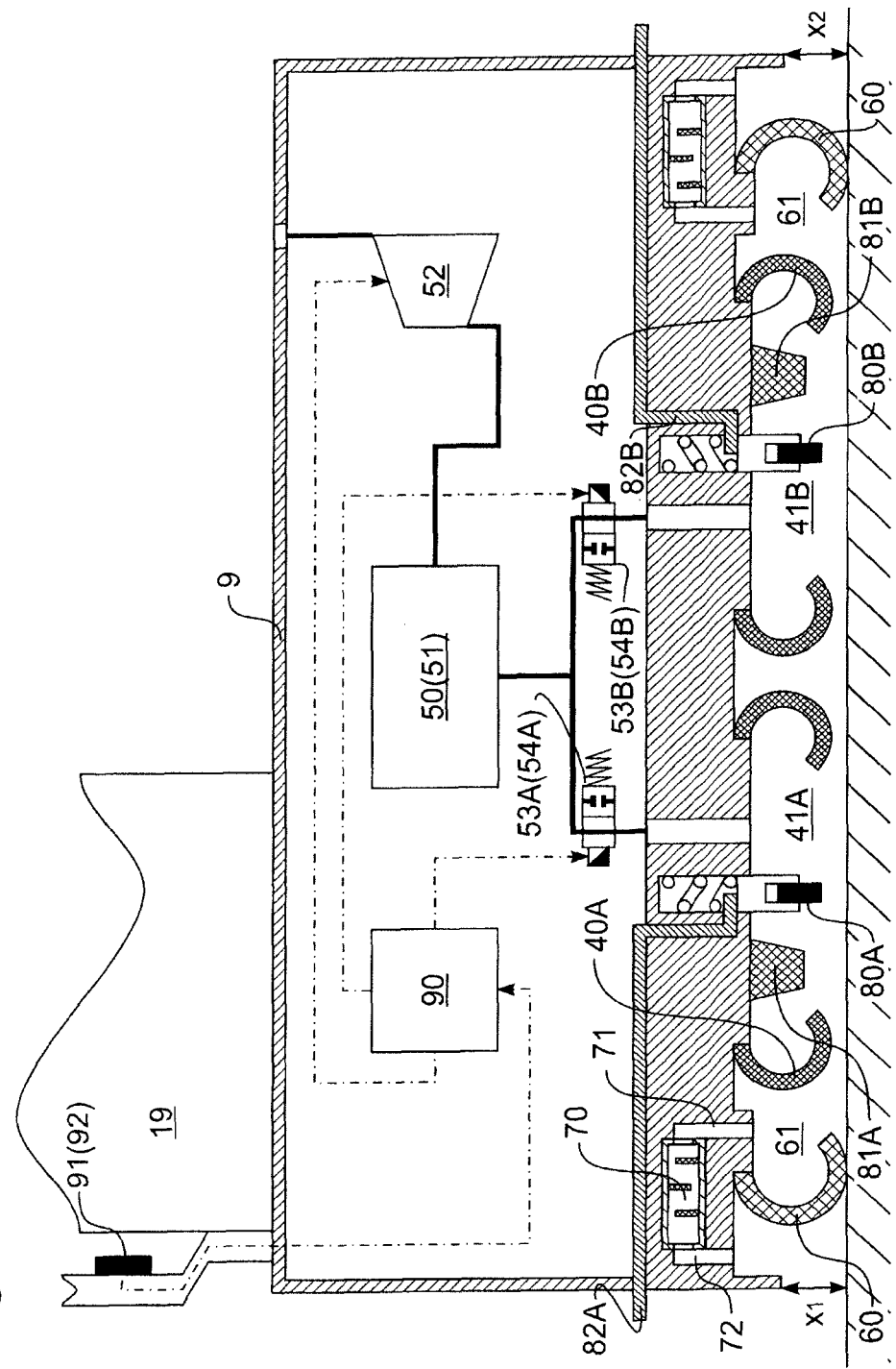
FIG. 12: shows a part of the carrier system from FIG. 11 in a cutaway view.

FIG. 12 shows a cutaway through a part of carrier 9. An air chamber arrangement, arranged thereon, comprises in the embodiment from FIG. 12 a pressure chamber 41A surrounded by a pressure apron 40A and a pressure chamber 41B surrounded by an additional pressure apron 40B, said pressure chambers are supplied independently from one another with compressed air from a compressed air supply via control valves 53A or 53B to form an air cushion. In the embodiment from FIG. 12, the compressed air supply comprises a carrier-side compressed air source with a turbomachine in the form of a compressor 52 and pressure accumulator in the form of a pressurized container 50 which is chargeable or charged by the compressor.

To move carrier 9, the user actuates an operating device in the form of an actuation button 91 which transmits this to a controller 90. This controller correspondingly opens valves 53A, 53B so that pressure chambers 41A, 41B are supplied or charged with compressed air from pressurized container 50 of the compressed air supply and carrier 9 is manually movable carried by means of the air cushion. In a way described subsequently with reference to FIG. 15, the controller thereby regulates the position of the valves. Additionally or alternatively, the controller may also control the compressor.

The compressed air, flowing through a gap between pressure aprons 40A, 40B and the floor, may thereby cause an undesired sound emission and dust swirling. Therefore, a common acoustic apron 60 surrounds a sound chamber 61 which surrounds pressure chambers 41A, 41B. Acoustic apron 60 is elastically biased against the floor and has a floor-side sealing lip.

Sound chamber 61 communicates via a passage 71 with a carrier-side sound damping means in the form of an absorption sound damper 70 for damping airborne sound in the sound chamber. The air, damped of sound in such a way, discharges via a passage 72 into the surroundings.

For fixing carrier 9, the user actuates another actuation button 92, which transmits this to a controller 90. This controller correspondingly closes valves 53A, 53B and closes off pressure chambers 41A, 41B from pressurized container 50 of the compressed air supply. Instead, the controller now analogously opens control valves 54A, 54B, which supply pressure chambers 41A, 41B with negative pressure from a negative pressure accumulator in the form of a negative pressure container 51 of a carrier-side negative pressure source of a negative pressure supply, which is evacuatable by reversibly-driven compressor 52. Thus, a negative pressure is formed in pressure chambers 51A, 51B which fix carrier 9 on the floor. In a way subsequently described with reference to FIG. 15, the controller thereby regulates the position of the valves. Additionally or alternatively, the controller may also control the compressor.

The carrier is thereby supported by a support arrangement with three or four elastic supports in pressure chambers 41A or 41B, of which two supports 81A, 81B are visible in the cutaway of FIG. 12.

The carrier system additionally comprises a roller arrangement, arranged stationarily on the carrier, with at least three transport rollers arranged in pressure chambers 41A, 41B, of which two transport rollers 80A or 80B are visible in the cutaway of FIG. 12. In the embodiment, these are biased by compression springs out of a storage position into an operating position, in which they protrude past supports 81A, 81B on the floor side. In the operating position, the transport rollers may be locked by a locking mechanism which blocks a retraction into the stored position. In contrast, upon releasing the locking mechanism, the transport rollers retract into their storage position so that the carrier rests on supports 81A, 81B if the air cushion is not formed. If, in contrast, the air cushion is formed, as is shown in FIG. 12, both the supports and also the transport rollers are spaced apart from the floor.

Figure 13:
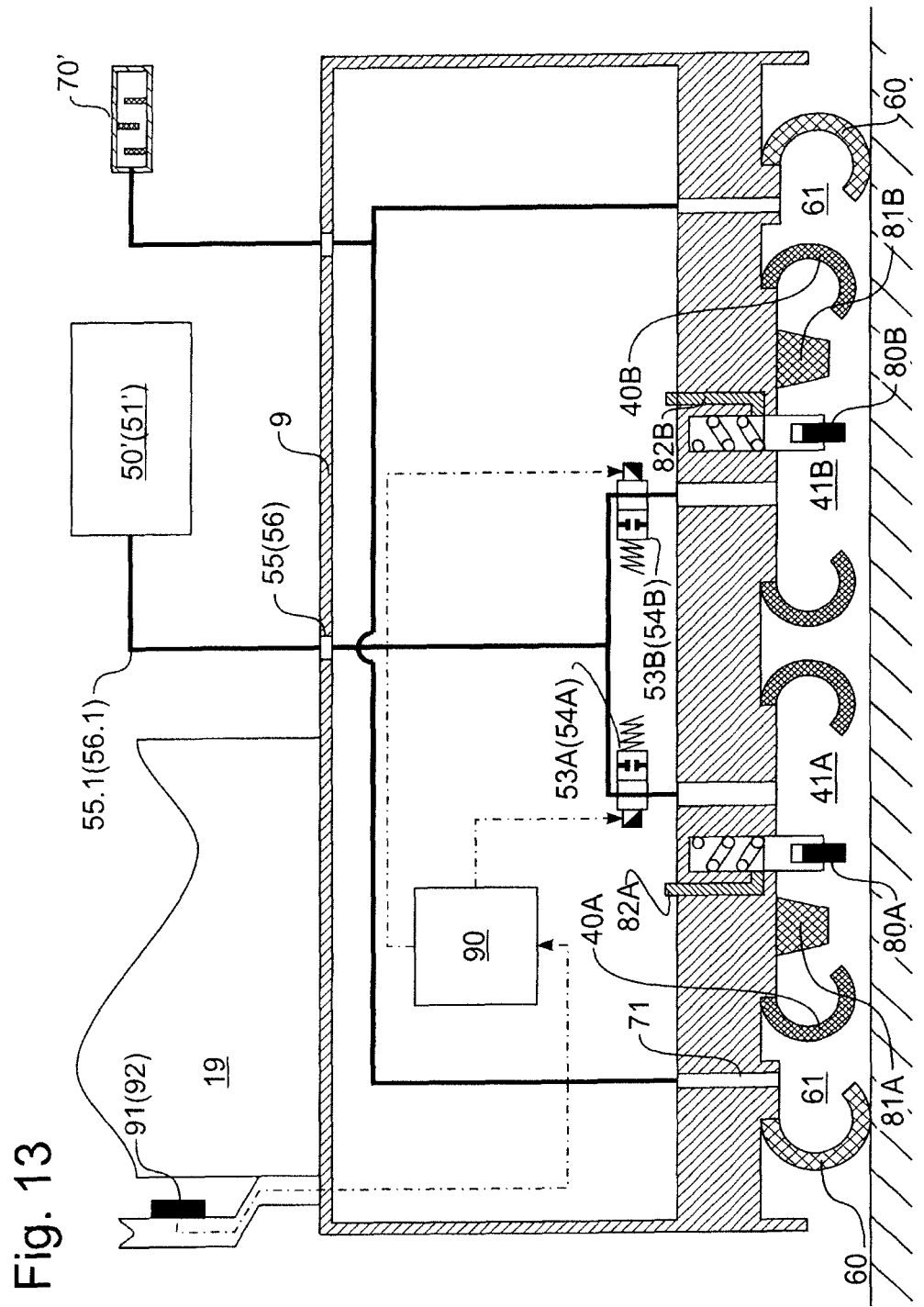
FIG. 13: shows a part of a carrier system according to another embodiment of the present invention corresponding to the view in FIG. 12.

FIG. 13 shows, in a way corresponding to FIG. 12, a carrier system according to another embodiment of the present invention. Features matching the previously described embodiment are identified by identical reference numerals so that reference is made to the previous description and subsequently only the differences are described.

In the embodiment from FIG. 13, the compressed air source in the form of a compressed air accumulator or pressurized container 50', the negative pressure source in the form of a negative pressure accumulator or negative pressure container 51', and the sound damping means in the form of an absorption sound damper 70' are all external to the carrier. Correspondingly, the compressed air supply has a carrier-side air duct connection 55 which is detachably connected to carrier-remote pressurized container 50' via a flexible duct 55.1, and the negative pressure supply has a carrier-side air duct connection 56 which is detachably connected to carrier-remote negative pressure container 51' via a flexible duct 56.1. Carrier-remote absorption sound damper 70' likewise communicates with sound chamber 61 via a flexible air duct connected to carrier 9 and guides compressed air out of carrier-remote sound chamber 61 and into the surroundings in a sound-damped way.

Figure 14:
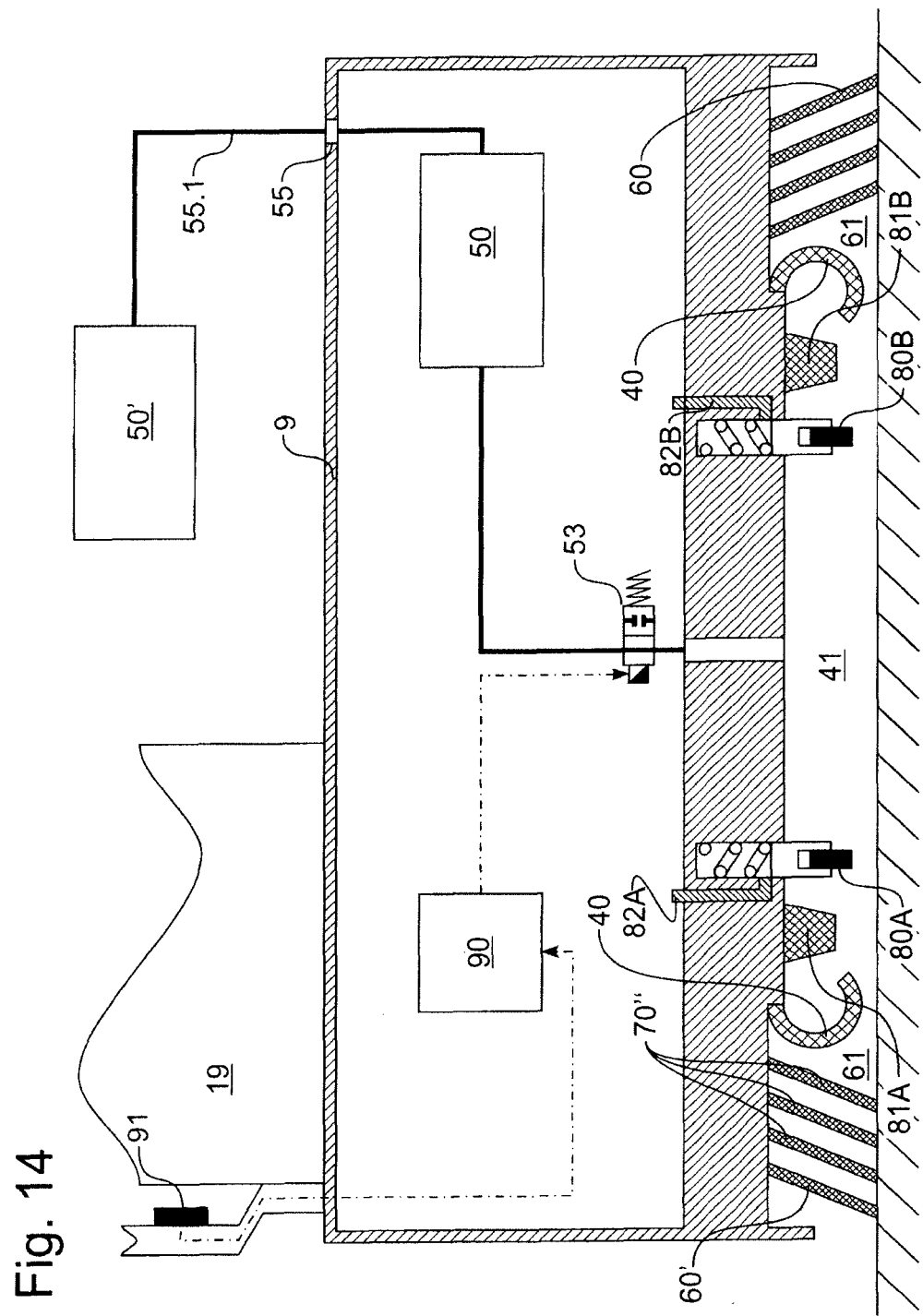
FIG. 14: shows a part of a carrier system according to another embodiment of the present invention corresponding to the view in FIGS. 12, 13.

FIG. 14 shows, in a way corresponding to FIGS. 12, 13, a carrier system according to another embodiment of the present invention. Features matching the previously described embodiment are identified by identical reference numerals so that reference is made to the previous description and subsequently only the differences are described.

In the embodiment from FIG. 14, the sound damping means is arranged in acoustic chamber 61 in the form of multiple concentric rows of lamellae 70", acoustic apron 60' is likewise formed as an (outermost) row of lamellae.

In addition, carrier-side pressurized container 50, which functions in particular as a buffer, is detachably connected on the one side to carrier-remote pressurized container 50' via carrier side air duct connection 55 and flexible duct 55.1 and is suppliable on the other side by control valve 53 with compressed air from the single pressure chamber 41, which is surrounded by pressure apron 40, in that controller 90 opens this valve as a result of a corresponding actuation of actuating button 91, in particular, opens or closes more strongly and/or longer for regulating the vertical distance to the floor.

Figure 15:
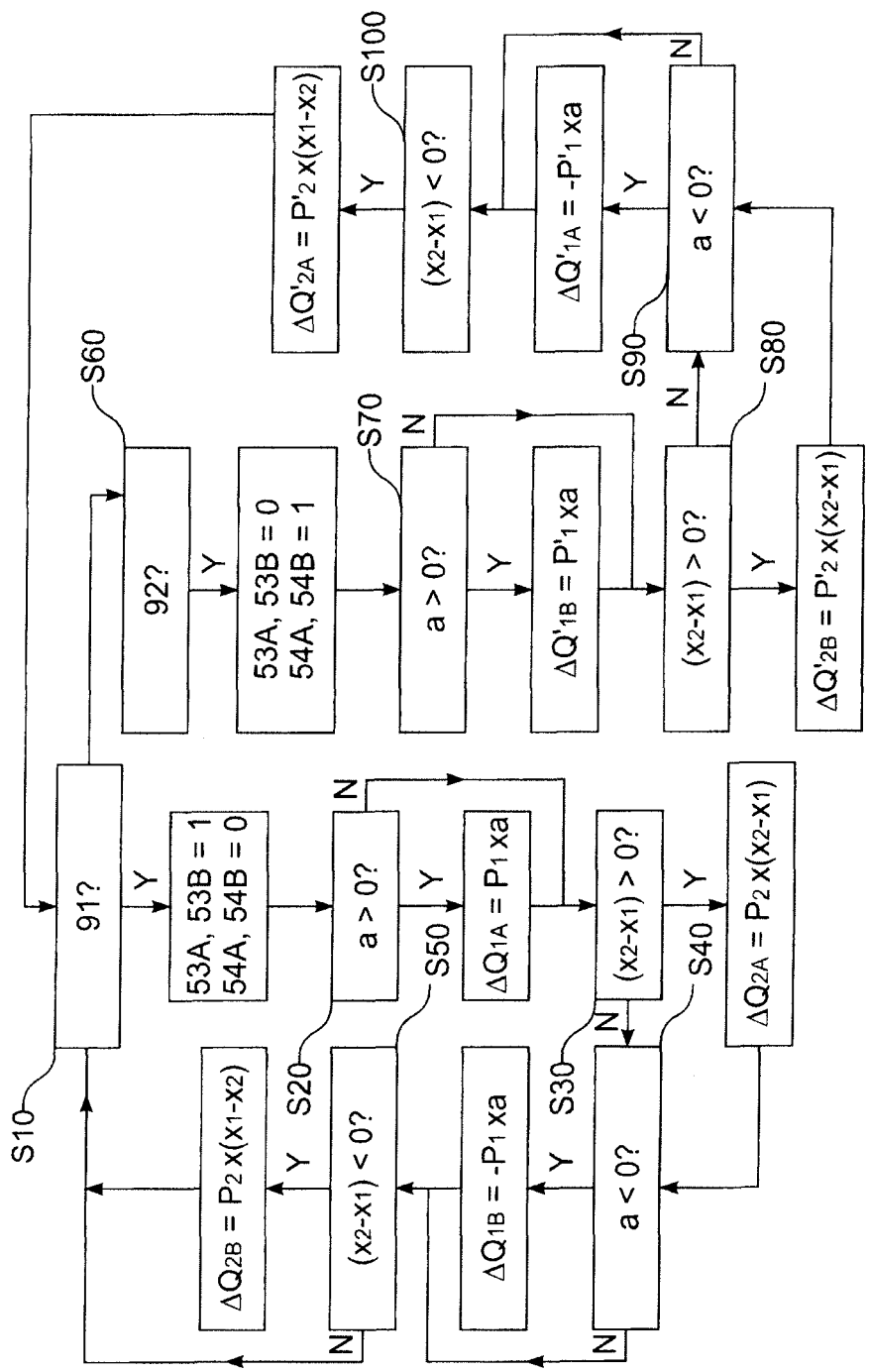
FIG. 15: shows a method for moving and/or fixing the carrier system from FIG. 13 according to one embodiment of the present invention.

Subsequently, a method for moving and/or fixing carrier 9 of the carrier system from FIG. 13, carrier out by controller 90, is described by way of example using FIG. 15

As long as the user actuates actuating button 91 (S10: "Y"), controller 90 opens valves 53A, 53B so that pressurized chambers 41A, 41B are supplied with compressed air from pressurized container 50 (S20).

Controller 90 thereby detects via detection means in the form of joint sensors (not shown) a pose of manipulator 10 and identifies from this the aligned or signed horizontal distance a, as an extension, of its flange 12 from a reference configuration free of tilting moment (compare FIG. 11). Furthermore, controller 90 detects via distance sensors on the near-ground corners of the carrier (not shown) an aligned or signed position and orientation or deflection to the horizontal $x_2-x_1$ of carrier 9 (compare FIG. 11).

Controller 90 increases the air supply Q to pressure chamber 41A by $\Delta Q_{1A}$ by correspondingly controlling valve 53A according to the control rule $\Delta Q_{1A}=P_1*a$ using the constant positive proportional factor $P_1$, as long as extension a is positive or is aligned with pressure chamber 41A (S20: "Y"), and by $\Delta Q_{2A}$ according to control rule $\Delta Q_{1A}=P_2*(x_2-x_1)$ using constant positive proportional factor $P_1$, as long as deflection $x_2-x_1$ is positive or is aligned with pressure chamber 41A (S30: "Y"). In an analogous way, controller 90 increases air supply Q to pressure chamber 41B by $\Delta Q_{1B}$ by correspondingly controlling valve 53B according to the control rule $\Delta Q_{1B}=-P_1*a$ as long as extension a is negative or is aligned with pressure chamber 41B (S40: "Y") and by $\Delta Q_{2B}$ according to control rule $\Delta Q_{1B}=P_2*(x_1-x_2)$ as long as deflection $x_2-x_1$ is negative or is aligned with pressure chamber 41B (S50: "Y").

If, in contrast, the user commands a fixing to the floor by actuating actuating button 92 (S60: "Y"), controller 90 closes valves 53A, 53B and opens valves 54A, 54B so that pressure chambers 41A, 41B are now supplied with negative pressure from negative pressure container 51.

Controller 90 increases the air extraction Q' from pressure chamber 41B by $\Delta Q'_{1B}$ by correspondingly controlling valve 54B according to the control rule $\Delta Q'_{1B}=P'_1*a$ using the constant positive proportional factor $P'_1$, as long as extension a is positive or is aligned with pressure chamber 41A (S70: "Y"), and by $\Delta Q'_{2B}$ according to control rule $\Delta Q'_{2B}=P'_2*(x_2-x_1)$ using constant positive proportional factor $P'_1$, as long as deflection $x_2-x_1$ is positive or is aligned with pressure chamber 41A (S80: "Y"). In an analogous way, controller 90 increases air extraction Q' from pressure chamber 41A by $\Delta Q'_{1A}$ by correspondingly controlling valve 54A according to the control rule $\Delta Q'_{1A}=-P'_1*a$ as long as extension a is negative or is aligned with pressure chamber 41B (S90: "Y") and by $\Delta Q'_{2A}$ according to control rule $\Delta Q'_{2A}=P'_2*(x_1-x_2)$ as long as deflection $(x_2-x_1)$ is negative or is aligned with pressure chamber 41B (S100: "Y").

Thus, controller 90 increases, on the basis of the detected pose of manipulator 10 and the detected position and orientation of carrier 9, the overpressure on one side, via which a tilting moment, which is induced by an extension a of the manipulator and functions against the horizontal in a deflection of the carrier, seeks to tilt the carrier system. Analogously, controller 90 increases, on the basis of the detected pose of manipulator 10 and the detected position and orientation of carrier 9, the underpressure on one side of the carrier system, which seeks to alleviate a tilting moment, which is induced by an extension a of the manipulator and functions against the horizontal in a deflection of the carrier.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

REFERENCES

1 Positioning device base
1, 4, 6; 24 Joints of the kinematic system
3, 5; 35 Links of the kinematic system
7 Positioning flange
8; 8' Compression spring (biasing means)
9 Carrier
10 Surgical robot
11 Surgical robot base
12 Surgical robot flange
13 End effector
14 Instrument shaft
17 Additional linear joint
17' Additional rotary joint
19 Rotatable lifting column
19.1 Linear axis
19.2 Linear-rotational axis
20 Slide
100; 101; 102 Mechanical positive coupling
201; 203; 204; 206 Rotary joints
202/205 First/Second coupling rods
301/303/305/307 First/Second/Third/Fourth
304/306 First/Second traction means
V; V' Virtual point of rotation
40; 40A, 40B Pressure chamber
41; 41A, 41B Pressure apron
50; 50' Pressurized container
51; 51' Negative pressure container
52 Compressor
53; 53A, 53B, 54A, 54B Control valve
55, 56 Air duct connection
55.1, 56.1' Air duct
60; 60' Acoustic apron
61 Sound chamber
70; 70'; 70" Sound damping means
71, 72 Passage
80A, 80B Transport roller
81A, 81B Support
90 Controller
91, 92 Actuating button
82A, 82B Locking mechanism

What is claimed is:

1. A positioning device for a robot having an end effector, the positioning device comprising:
    a base;
    a flange adapted to couple with the robot, wherein the flange is connected to the base by a kinematic system comprising at least two joints;
    the flange adjustable relative to the base by the kinematic system from a first position to a second position spaced apart from the first position; and
    an orientation means for reorienting the flange from a first orientation in the first position into a second orientation in the second position as a result of the adjustment from the first position into the second position;
    wherein the kinematic system comprises three rotary joints arranged in series connecting the base and the flange, the three rotary joints connecting the base and the flange having parallel axes of rotation wherein a four-bar guide mechanism is formed by the orientation means;
    the four-bar guide mechanism comprising the serially arranged rotary joints of the kinematic system and one virtual point of rotation that is stationary relative to the base, with parallel axes or rotation.

2. The positioning device of claim 1, wherein at least one of:
    the end effector of the robot is a surgical end effector;
    the flange is adjustable from the first position to the second position at least substantially on a circular path or a straight line; or
    the second orientation is rotated relative to the first orientation about a reference axis by at least 75 degrees.

3. The positioning device of claim 1, wherein:
    the flange is further adjustable relative to the base by the kinematic system into at least one intermediate position between the first position and the second position; and
    the orientation means is further configured to reorient the flange into an intermediate orientation in the intermediate position as a result of an adjustment from the first or second position into the intermediate position.

4. The positioning device of claim 3, wherein the intermediate orientation is rotated about the reference axis in a range of about 25 degrees to about 60 degrees relative to at least one of the first orientation or the second orientation.

5. The positioning device of claim 1, wherein the kinematic system comprises at least one of:
    at least one rotary joint; or
    at least one linear joint.

6. The positioning device of claim 5, wherein the at least one rotary joint comprises at least three rotary joints.

7. The positioning device of claim 6, wherein at least one of:
    the at least three rotary joints are arranged in series; or
    the at least three rotary joints have parallel axes of rotation.

8. The positioning device of claim 1, wherein the orientation means comprises at least one mechanical coupling of two links of the positioning device which are connected to one another by at least one joint of the kinematic system.

9. The positioning device of claim 8, wherein the at least one mechanical coupling is a detachable mechanical coupling.

10. The positioning device of claim 8, wherein the mechanical coupling comprises a transmission.

11. The positioning device of claim 10, wherein the transmission comprises one of a gear train, a traction gear, a worm gear, a cam gear, a coupling gear, a connecting rod transmission, a coupling rod transmission, or a hydraulic transmission.

12. The positioning device of claim 1, wherein the four-bar guide mechanism is a parallelogram guide arrangement.

13. The positioning device of claim 1, wherein the kinematic system that connects the base and the flange comprises a linear joint and a rotary joint connected thereto; and
wherein the orientation means comprises a mechanical coupling of the base and the flange.

14. The positioning device of claim 1, wherein at least one joint of the kinematic system has a locking mechanism for locking of the respective joint.

15. The positioning device of claim 14, wherein all joints of the kinematic system have a locking mechanism for locking the respective joint.

16. The positioning device of claim 14, wherein locking of the locking mechanism is at least one of mechanical, manual, or actuated.

17. The positioning device of claim 14, wherein the at least one joint is one of:
lockable together with at least one other joint of the kinematic system; or
lockable independently of at least one other joint of the kinematic system.

18. The positioning device of claim 1, further comprising:
a biasing means that binds two links of the positioning device that are connected to one another by at least one joint of the kinematic system;
wherein the biasing means is more strongly biased by a movement of the positioning device into a pose in which the positioning device has a lower positional energy.

19. The positioning device of claim 18, wherein the biasing means is at least one of a mechanical biasing means or a pneumatic biasing means.

20. The positioning device of claim 1, wherein the positioning device comprises at least two links connected to one another by at least one joint of the kinematic system;
the at least two links convertible into a storage position wherein the at least two links are in a folded arrangement to be at least substantially parallel to one another.

21. The positioning device of claim 1, further comprising a carrier on which the base is mounted such that the base is at least one of:
linearly moveable in one or more axes; or
rotatable in one or more axes.

22. A robot arrangement, comprising:
a positioning device, comprising:
a base,
a flange adapted to receive a robot, wherein the flange is connected to the base by a kinematic system comprising at least two joints,
the flange adjustable relative to the base by the kinematic system from a first position to a second position spaced apart from the first position, and
an orientation means for reorienting the flange from a first orientation in the first position into a second orientation in the second position as a result of the adjustment from the first position into the second position,
wherein the kinematic system comprises three rotary joints arranged in series connecting the base and the flange, the three rotary joints connecting the base and the flange having parallel axes of rotation wherein a four-bar guide mechanism is formed by the orientation means,
the four-bar guide mechanism comprising the serially arranged rotary joints of the kinematic system and one virtual point of rotation that is stationary relative to the base, with parallel axes or rotation; and
a robot with an end effector, the robot secured to the flange.

23. The robot arrangement of claim 22, wherein at least one of:
the end effector of the robot is a surgical end effector;
the flange is adjustable from the first position to the second position at least substantially on a circular path or a straight line; or
the second orientation is rotated relative to the first orientation about a reference axis by at least 75 degrees.

24. The robot arrangement of claim 22, wherein the robot is at least one of:
detachably secured on the flange;
rigidly secured on the flange;
secured linearly moveably on the flange; or
rotatably secured on the flange.

25. A method for positioning a robot of a robot arrangement, the robot arrangement including a robot with an end effector and a positioning device, the positioning device comprising a base; a flange coupled with the robot, wherein the flange is connected to the base by a kinematic system comprising at least two joints and wherein the flange is adjustable relative to the base by the kinematic system from a first position to a second position spaced apart from the first position; and an orientation means for reorienting the flange from a first orientation in the first position into a second orientation in the second position as a result of the adjustment from the first position into the second position, wherein the kinematic system comprises three rotary joints arranged in series connecting the base and the flange, the three rotary joints connecting the base and the flange having parallel axes of rotation wherein a four-bar guide mechanism is formed by the orientation means, the four-bar guide mechanism comprising the serially arranged rotary joints of the kinematic system and one virtual point of rotation that is stationary relative to the base, with parallel axes or rotation, the method comprising:
adjusting the flange from a first position to a second position with the kinematic system; and
reorienting the flange with the orientation means from a first orientation to a second orientation as a result of the adjustment.

* * * * *